US00RE47057E

(19) United States
(12) Reissued Patent
Sarwal et al.

(10) Patent Number: US RE47,057 E
(45) Date of Reissued Patent: Sep. 25, 2018

(54) METHODS AND COMPOSITIONS FOR EVALUATING GRAFT SURVIVAL IN A SOLID ORGAN TRANSPLANT RECIPIENT

(75) Inventors: Minnie M. Sarwal, Portola Valley, CA (US); Elaine S. Mansfield, Sunnyvale, CA (US)

(73) Assignee: The Board of Trustees of the Leland Stanford Junior University, Stanford, CA (US)

(21) Appl. No.: 13/529,768

(22) Filed: Jun. 21, 2012

Related U.S. Patent Documents

Reissue of:
(64) Patent No.: 7,741,038
Issued: Jun. 22, 2010
Appl. No.: 11/375,681
Filed: Mar. 13, 2006

U.S. Applications:
(60) Provisional application No. 60/662,083, filed on Mar. 14, 2005.

(51) Int. Cl.
*C12Q 1/68* (2018.01)
*G01N 33/53* (2006.01)
*C12Q 1/6883* (2018.01)
*C12Q 1/6876* (2018.01)

(52) U.S. Cl.
CPC ..... *C12Q 1/6883* (2013.01); *C12Q 1/6876* (2013.01); *C12Q 2600/106* (2013.01); *C12Q 2600/118* (2013.01); *C12Q 2600/158* (2013.01)

(58) Field of Classification Search
CPC ..... C12Q 1/6883
See application file for complete search history.

(56) References Cited

U.S. PATENT DOCUMENTS

| | | | |
|---|---|---|---|
| 6,607,879 | B1 | 8/2003 | Cocks et al. |
| 7,026,121 | B1 | 4/2006 | Wohlgemuth et al. |
| 7,879,556 | B2 | 2/2011 | Wohlgemuth et al. |
| 2003/0007968 | A1 | 1/2003 | Larsen et al. |
| 2003/0017619 | A1 | 1/2003 | Rokubo et al. |
| 2003/0022252 | A1 | 1/2003 | Thomson |
| 2003/0104371 | A1 | 6/2003 | Strom et al. |
| 2004/0163654 | A1 | 8/2004 | Williams |
| 2005/0025769 | A1 | 2/2005 | Kobayashi et al. |
| 2006/0073496 | A1 | 4/2006 | O'Toole et al. |
| 2006/0088836 | A1 | 4/2006 | Wohlgemuth et al. |
| 2006/0088876 | A1 | 4/2006 | Bauer |
| 2006/0246485 | A1 | 11/2006 | Sarwal et al. |
| 2006/0269949 | A1 | 11/2006 | Halloran et al. |
| 2006/0281122 | A1 | 12/2006 | Bryant et al. |
| 2007/0031890 | A1 | 2/2007 | Wohlgemuth et al. |
| 2007/0111210 | A1 | 5/2007 | Bigaud et al. |
| 2007/0122806 | A1 | 5/2007 | Strom et al. |
| 2007/0134261 | A1 | 6/2007 | Hancock et al. |
| 2007/0134728 | A1 | 6/2007 | Hu et al. |
| 2007/0212701 | A1 | 9/2007 | O'Toole et al. |
| 2007/0232658 | A1 | 10/2007 | Wagner et al. |
| 2007/0264272 | A1 | 11/2007 | Perreault et al. |
| 2008/0233573 | A1 | 9/2008 | Storm et al. |
| 2008/0274906 | A1 | 11/2008 | Cappola et al. |
| 2008/0280282 | A1 | 11/2008 | Bauer, Jr. |
| 2008/0305493 | A1 | 12/2008 | Strovel et al. |
| 2009/0022730 | A1 | 1/2009 | Raulf et al. |
| 2009/0155784 | A1 | 6/2009 | O'Toole et al. |
| 2009/0197286 | A1 | 8/2009 | Karin et al. |
| 2009/0220518 | A1 | 9/2009 | Dinarello et al. |
| 2009/0232825 | A1 | 9/2009 | Gorczynski et al. |
| 2009/0269334 | A1 | 10/2009 | Bigaud et al. |
| 2009/0304705 | A1 | 12/2009 | Grass |
| 2009/0324618 | A1 | 12/2009 | Armstrong et al. |
| 2010/0120629 | A1 | 5/2010 | Ellis et al. |
| 2010/0234292 | A1 | 9/2010 | Bertucci et al. |
| 2010/0304987 | A1 | 12/2010 | Sanchez Fueyo et al. |
| 2010/0305188 | A1 | 12/2010 | Nakano et al. |
| 2011/0064709 | A1 | 3/2011 | Miller et al. |
| 2011/0171645 | A1 | 7/2011 | McManus et al. |
| 2011/0189680 | A1 | 8/2011 | Keown et al. |
| 2011/0201519 | A1 | 8/2011 | Sarwal et al. |
| 2013/0157888 | A1 | 6/2013 | Nagele |

FOREIGN PATENT DOCUMENTS

| | | |
|---|---|---|
| EP | 1731620 | 12/2006 |
| EP | 2295966 | 3/2011 |
| WO | 2004/074815 | 9/2004 |
| WO | 2005/005601 | 1/2005 |

(Continued)

OTHER PUBLICATIONS

Agilent-014850 whole human genome microarray 4×44K G4112F (Probe Name Version), GEO (2008), XP002594592.
Brouard; et al., "Identification of a peripheral blood transcriptional biomarker panel associated with operational renal allograft tolerance", PNAS (Sep. 2007), 104(39):15448-15453.
Carvalho-Gaspar; et al., "Chemokine gene expression during allograft rejection: Comparison of two quantitative PCR techniques", Journal of Immunological Methods (Jun. 2005), 301(1-2):41-52.
Chan, "Integrating Transcriptomics and Proteomics", Drug Discovery and Development (Apr. 2006), printed from www.ddmag.com, 6 pages.
Chen; et al., "Discordant protein and mRNA expression in lung adenocarcinomas", Molecular and Cellular Proteomics (Apr. 2002), 1(4):304-13.
Cheung; et al., "Natural Variation in Human Gene Expression Assessed in Lymphoblastoid Cells", Nature Genetics (Mar. 2003), 33:422-425.
Chu; et al., "Cloning of a new "finger" protein gene (ZNF173) within the class I region of the human MHC", Genomics (Sep. 1995), 29(1):229-39.

(Continued)

*Primary Examiner* — Johnny F Railey
(74) *Attorney, Agent, or Firm* — Kyle A. Gurley; Bret E. Field; Bozicevic, Field & Francis LLP

(57) ABSTRACT

Methods are provided for evaluating a subject for graft survival, e.g., in terms of predicting graft survival, identifying the presence of a deleterious graft condition, such as CAN and DT, identifying the severity and class of acute rejection, etc, in a subject are provided. In practicing the subject methods, the expression of at least one gene in a sample from the subject, e.g., a blood or biopsy sample, is assayed, e.g., at the nucleic acid and/or protein level, to evaluate the subject. Also provided are compositions, systems and kits that find use in practicing the subject methods. The methods and compositions find use in a variety of applications.

20 Claims, 4 Drawing Sheets

(56) References Cited

FOREIGN PATENT DOCUMENTS

| | | |
|---|---|---|
| WO | 2005/070086 | 8/2005 |
| WO | WO2006099421 | 9/2006 |
| WO | 2007/104537 | 9/2007 |
| WO | 2007/121922 | 11/2007 |
| WO | 2008/009132 | 1/2008 |
| WO | 2008/084331 | 7/2008 |
| WO | 2009/143624 | 12/2009 |
| WO | WO2010083121 | 7/2010 |
| WO | 2010/038974 | 8/2010 |

OTHER PUBLICATIONS

Database Embl [Online], "Thymidine Kinase, Cytosolic (human), mRNA Sequence", (1998), 2pages, XP002434108, Database accession No. AA778098.
Dugré; et al., "Cytokine and cytotoxic molecule gene expression determined in peripheral blood mononuclear cells in the diagnosis of acute renal rejection.", Transplantation (Oct. 2000), 70(7):1074-1080.
Enard; et al., "Intra- and interspecific variation in primate gene expression pattems", Science (Apr. 2002), 296 (5566):340-3.
Farivar; et al., "The role of CC and CXC chemokines in cardiac allograft rejection in rats", Experimental and Molecular Pathology (Jun. 2005), 78(3):171-176.
Flechner; et al., "Kidney transplant rejection and tissue injury by gene profiling of biopsies and peripheral blood lymphocytes", American Journal of Transplantation (Sep. 2004), 4(9):1475-89.
Fujiwaki; et al., "Thymidine Kinase in Epitheliar Ovarian Cancer: Relationship with the Other Pyrimidine Pathway Enzymes", Int. J. Cancer (May 2002), 99(3):328-335.
Gimino; et al., "Gene Expression Profiling of Broncholveolar Lavage Cells in Acute Lung Rejection", American Journal of Respiratory and Critical Care Medicine (Nov. 2003), 168:1237-1242.
Gronowitz; et al., "Serum Thymidine Kinase in Transplant Patients: Its Relation to Cytomegalovirus Activity, Renal Transplant Rejection and its Use for Monitoring of Antiviral Therapy", Annals of Clinical Research (1986), 18(2):71-75.
Hernandez-Fuentes; et al., "Immunologic monitoring", Immunological Reviews (Dec. 2003), 196:247-264.
Horwitz; et al., "Detection of Cardiac Allograft Rejection and Response to Immunosuppressive Therapy with Peripheral Blood Gene Expression", Circulation (Dec. 2004), 110:3815-3821.
Jevnikar; et al., "Late Kidney Allograft Loss: What We Know About It, and What We Can Do About It", Clin J Am Soc Nephrol (Mar. 2008), 3(S56-S67).
Joosten; et al., "Chronic Renal Allograft Rejection: Pathophysiologic Considerations", Kidney International (Jul. 2005), 68:1-13.
Lee et al., "Expression profiling of murine double-negative regularoty T cells suggest mechanisms for prolonged cardiac allograft survival", J. Immunol. (Apr. 2005), 174(8):4535-4544.
Li; et al., "Identifying compartment-specific non-HLA targets after renal transplantation by integrating transcriptome and "antibodyome" measures", PNAS (Mar. 2009), 106(11):4148-4153.
Marsden, "Predicting Outcomes after Renal Transplantation—New Tools and Old Tools", The New England Journal of Medicine (Jul. 2003), 349(2):182-184.
Martinez-Llordella; et al., "Using transcriptional profiling to develop a diagnostic test of operational tolerance in liver transplant recipients", The Journal of Clinical Investigations (Aug. 2008), 118(8):2845-2857.
McMorrow; et al., "New intra-renal graft genes associated with tolerance or rejection", Kidney International, symp. 1 (Jan. 2002), 61: 885-S93.
Medbury; et al., "The Cytokine and Histological Response in Islet Xenograft Rejection is Dependent Upon Species Combination", Transplantation (Nov. 1997), 64(9):1307-1314.
Midha; et al., "Chemokine Expression in Nerve Allografts", Neurosurgery (Jun. 2004), 54(6):1472-149.
O'Riordan; et al., "Bioinformatic Analysis of the Urine Proteome of Acute Allograft Rejection", Journal of American Society of Nephrology (Dec. 2004), 15:3240-3248.
Sarwal; et al., "Integrative Genomics to Identify Non-HLA Allogenic Kidney-Specific Targets after Kidney Transplantation", Transplantation (2008), 86(2S):13, Oral Abstracts, downloaded Apr. 6, 2010.
Sarwal; et al., "Molecular Heterogeneity in Acute Renal Allograft Rejection Identified by DNA Microarray Profiling", New England Journal of Medicine (Jul. 2003), 349:125-138.
Serody; et al., "T-lymphocyte production of macrophage inflammatory protein-lalpha is critical to the recruitment of CD8(+) T cells to the liver, lung, and spleen during graft-versus-host disease", Blood (Nov. 2000), 96(9):2973-2980.
Shi; et al., "[Clinical significance of Rantes and MIP-1 alpha in acute rejection episode in kidney transplantation]", Zhongguo Yi Xue Ke Xue Yuan Xue Bao (Feb. 2004), abstract.
Simon; et al., "Serial Peripheral Blood Perforin and Granzyme B Gene Expression Measurements for Prediction of Acute Rejection in Kidney Graft Recipients", American Journal of Transplantation (Sep. 2003), 3:1121-1127.
Teramoto; et al., "DNA Synthesis in Hepatocytes During Liver Allograft Rejection in Rats", Transplantation (Aug. 1990), 50(2):199-201.
Thomson; et al., "Monitoring the Patient Off Immunosuppression", Transplantation (Oct. 2001), 72(8):S13-S22.
Wakui; et al., "Genes Highly Expressed in the Early Phase of Murine Graft-Versus-Host Reaction", Biochemical and Biophysical Communications (Mar. 2001), 282:200-206.
Whitfield; et al., "Systemic and Cell Type-Specific Gene Expression Patterns in Scleroderma Skin", Proc. Natl. Acad Sci. (Oct. 2003), 100(21):12319-12324.
Wu, "Analysing Gene Expression Data From DNA Microarrays to Identify Candidate Genes", Journal of Pathology (Sep. 2001), 195:53-65.
Zhang; et al., "Microarray Analysis of Gene Expression in Peripheral Blood Mononuclear Cells Derived From Long-Surviving Renal Recipients", Transplantation Proceedings (Aug. 2002), 34:1757-1759.
Alarcon; et al. "Time to renal disease and end-stage renal disease in Profile: a multiethnic lupus cohort", PLos Med (Oct. 2006), 3(10):e396.
Gwinner; et al. "Renal transplant rejection markers." World J Urol (Oct. 2007), 25(5):445-455.
Lang; et al. "DUSP meet immunology: dual specificity MAPK phosphatases in control of the inflammatory response", J Immunol (Dec. 2006), 177(11)1497-504.
Ling; et al. "Integrative urinary peptidomics in renal transplantation identifies biomarkers for acute rejection", J Am Soc Nephrol (Apr. 2010), 21(4):646-653.
Rotondi; et al. "High pretransplant serum levels of CXCL9 are associated with increased risk of acute rejection and graft failure in kidney graft recipients", Transpl Int (May 2010), 23(5):465-475.
Sigdel; et al. "Shotgun proteomics identifies proteins specific for acute renal transplant rejection", Proteomics Clin Appl (Jan. 2010), 4(1):32-47.
Voshol; et al. "Evaluation of biomarker discovery approaches to detect protein biomarkers of acute renal allograft rejection", J Proteome Res (Jul.-Aug. 2005), 4(4):1192-1199.
Communal; et al. "Reciprocal modulation of mitogen-activated protein kinases and mitogen-activated protein kinase phosphatase 1 and 2 in failing human myocardium", J Cardiac Failure (Apr. 2002), 8(2):86-92.
Akalin; et al., "Bocking Cell Microtubule Assembly Inhibits the Alloimmune Response In Vitro and Prolongs Renal Allograft Survival by Inhibition of Th1 and Sparing of Th2 Cell Function In Vivo", Journal of the American Society of Nephrology (1995), 5(7):1418-1425.
Braud; et al., "Immunosuppresive Drug-Free Operational Immune Tolerance in Human Kidney Transplant Recipients: Part 1. Blood Gene Expression Statistical Analysis", Journal of Cellular Biochemistry (Apr. 2008),103(6):1681-1692.

(56) References Cited

OTHER PUBLICATIONS

Hauge; et al., "Characterization of the FAM110 gene family", Genomics (May 2007), 90:14-27.
Hillier; et al., "Generation and annotation of the DNA sequences of human chromosomes 2 and 4", Nature (2005), 434:724-731.
Matsuki; et al., "Novel regulation of MHC class II function in B cells", The EMBO Journal (Jan. 2007), 26:846-854.
Saint-Mezard; et al., "Analysis of independent microarray datasets of renal biopsies identifies a robust transcript signature of acute allograft rejection", Transplant International (Mar. 2009), 22(3):293-302.
Roedder; et al., "The pits and pearls in translating operational tolerance biomarkers into clinical practice", Current Opinion in Organ Transplantation (Dec. 2012), 17(6):655-662.
Butte; et al., "Protein microarrays discover angiotensinogen and PRKRIP1 as novel targets for autoantibodies in chronic renal disease", Mol Cell Proteomics (Mar. 2011), 10(3):M110.000497.
Cox; et al., "Altered modulation of WNT-beta-catenin and PI3K/Akt pathways in IgA nephropathy", Kidney Int (Aug. 2010), 78(4):396-407.
Dinarello; et al., "Anti-inflammatory Agents: Present and Future", Cell (Mar. 2010), 140(6):935-950.
Ismail; "Important fluorinated drugs in experimental and clinical use", Journal of Fluorine Chemistry (Dec. 2002), 118(1):27-33.
Kalil; et al., "Meta-analysis: the efficacy of strategies to prevent organ disease by cytomegalovirus in solid organ transplant recipients", Ann Intern Med (Dec. 2005), 143(12):870-880.
Kaposztas; et al., "Impact of rituximab therapy for treatment of acute humoral rejection", Clin Transplant (Jan.-Feb. 2009), 23(1):63-73.
Li; et al., "A Peripheral Blood Diagnostic Test for Acute Rejection in Renal Transplantation", American Journal of Transplantation (Oct. 2012), 12(10):2710-2718.
Metz; et al., "Application of proteomics in the discovery of candidate protein biomarkers in a diabetes autoantibody standardization program sample subset", J Proteome Res (Feb. 2008), 7(2):698-707.
Sato; et al. "Aberrant CD3- and CD3-mediated signaling events in cord blood T Cells are associated with dysfunctional regulation of Fas ligand-mediated cytotoxicity", The Journal of Immunology (Apr. 1999), 162 (8):4464-4471.
Sigdel; et al., "Profiling of autoantibodies in IgA nephropathy, an integrative antibiomics approach", Clin J Am Soc Nephrol (Dec. 2011), 6(12):2775-2784.
"Affymetrix Human Genome U133 Plus 2.0 Array", Gene Expression Omnibus (Nov. 2003), XP002627319, 3 pgs.
Al-Lamki; et al., "Expression of Tumor Necrosis Factor Receptors in Normal Kidney and Rejecting Renal Transplants", Laboratory Investigation (Nov. 2001), 81(11):1503-1515.
Chen; et al., "Differentially Expressed RNA from Public Microarray Data Identifies Serum Protein Biomarkers for Cross-Organ Transplant Rejection and Other Conditions", PLOS Computational Biology (Sep. 2010), 6(9):e1000940.
Hardiman, "Microarray platforms—comparisons and contrasts", Pharmacogenomics (Jan. 2004), 5(5): 487-502.
Hauser; et al., "Prediction of Acute Renal Allograft Rejection by Urinary Monokine Induced by IFn-gamma (MIG)", The American Society of Nephrology (Jan. 2005), 16(6):1849-1858.
Hidalgo; et al., "The Transcriptome of Human Cytotoxic T Cells: Measuring the Burden of CTL-Associated Transcripts in Human Kidney Transplants", American Journal of Transplantation (Mar. 2008), 8(3):637-646.
Mengel; et al., "Scoring Total Inflammation Is Superior to the Current Banff Inflammation Score in Predicting Outcome and the Degree of Molecular Disturbance in Renal Allografts", American Journal of Transplantation (Aug. 2009), 9(8):1859-1867.
Morgun; et al., "Molecular Profiling Improves Diagnoses of Rejected and Infection in Transplanted Organs", Circulation Research (Jun. 2006), 98(12):e74-83.
Nesslinger; et al., "A viral vaccine encoding prostate-specific antigen induces antigen spreading to a common set of self-proteins in prostate cancer patients", Clinical Cancer Research (Aug. 2010), 16(15):4046-4056.
Gerrits; et al., "Donor-reactive cytokine production after HLA-identical living related kidney transplantation: a protein-array analysis", (Nov. 2006), 38(9):2825-7.
Joosten; et al., "Antibody response against the glomerular basement membrane protein agrin in patients with transplant glomerulopathy", American Journal of Transplantation (Feb. 2005), 5(2):383-93.
Mizutani; et al., "Frequency of MIC antibody in rejected renal transplant patients without HLA antibody", Human Immunology (Mar. 2006), 67(3):223-9.
Kazutoshi Takahashi et al: "Induction of Pluripotent Stem Cells from Adult Human Fibroblasts by Defined Factors", Cell, Cell Press, US, vol. 131, No. 5, Nov. 30, 2007 (Nov. 30, 2007), pp. 861-872.
Shiro, "Organ Transplant and Molecular Pathology", Journal of the Japan Society for Transplantation, (2004), 39, [2], p. 138-144.
Anglicheau et al. "Noninvasive Prediction of Organ Graft Rejection and Outcome Using Gene Expression Patterns", Transplantation, vol. 86, No. 2, Jul. 27, 2008, pp. 192-199.
Famulski; et al., "Changes in the Transcriptome in Allograft Rejection: IFN-.gamma.-Induced Transcripts in Mouse Kidney Allografts", American Journal of Transplantation (Jun. 2006), 6(6):1342-1354.
"GeneChip 3' IVT PLUS Reagent Kit", Affymetrix (2013), User Manual, 45 pgs.
Patil et al. "Bronchoalveolar Lavage Cell Gene Expression in Acute Lung Rejection: Development of a Diagnostic Classifier", Transplantation, Jan. 27, 2008, vol. 85, No. 2, pp. 224-231.
Hartono et al. "Noninvasive Diagnosis of Acute Rejection of Renal Allografts", Current Opinion in Organ Transplantation, vol. 15, No. 1, Feb. 2010, pp. 35-41.
First Examination Report for India patent application serial No. 9066/CHENP/2012, dated Feb. 26, 2018, translation letter reporting office action dated Mar. 19, 2018, 13 pages.
Alizadeh A. et al. Nature, vol. 403, Feb. 3, 2000, p. 503-511.
List of cDNA clones on the Lymphochip (2000), truncated from the fullist available online at https://llmpp.nih.gov/lymphoma/data/clones.xls, one printed page.
Godfrey T.E. et al., Journal of Molecular Diagnostics, vol. 2, No. 2, May 2000.
Hopfner R. et al., Cancer Research 60, 121-128, Jan. 1, 2000.
NCB I Gene output for UHRF1, from https://www.ncbi .nlm.nih.gov/gene/29128, printed on May 1, 2018, pp. 1-10.
Akalin, Enver; et al., "Gene expression analysis in human renal allograft biopsy samples using high-density oligoarray technology", Transplantation, Sep. 15, 2001, 72(5):948-53, XP002371138 ISSN: 0041-1337.
Chua, Mei-Sze; et al., "Applications of Microarrays to Renal Transplantation: Progress and Possibilities" Frontiers in Bioscience, Sep. 2003, 8:S913-23, XP008071504 ISSN: 1093-9946.
Mansfield, Elaine S.; et al., "Arraying the Orchestration of Allograft Pathology", American Journal of Transplantation, Jun. 2004, 4(6):853-62, XP002473233 ISSN:1600-6135.
Scherer Andreas; et al., "Early Prognosis of the Development of Renal Chronic Allograft Rejection by Gene Expression Profiling of Human Protocol Biopsies", Transplantation, Apr. 27, 2003, 75(8):1323-30, XP009045201 ISSN: 0041-1337.

METHODS AND COMPOSITIONS FOR EVALUATING GRAFT SURVIVAL IN A SOLID ORGAN TRANSPLANT RECIPIENT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

*Notice: More than one reissue application has been filed for the reissue of U.S. Pat. No. 7,741,038. The reissue applications are application Ser. No. 13/529,768 (the present application), and Ser. No. 13/943,626, filed Jul. 16, 2013 (a continuation reissue application).*

[Pursuant to 35 U.S.C. §119 (e), this application] *This application is a Reissue of U.S. Pat. No. 7,741,038, which patent issued on Jun. 22, 2010, and which patent* claims priority to the filing date of U.S. Provisional Patent Application Ser. No. 60/662,083 filed on Mar. 14, 2005; the disclosure of which application is herein incorporated by reference.

BACKGROUND

Transplantation of a graft organ or tissue from a donor to a host patient is a feature of certain medical procedures and treatment protocols. Despite efforts to avoid graft rejection through host-donor tissue type matching, in transplantation procedures where a donor organ is introduced into a host, immunosuppressive therapy is generally required to the maintain viability of the donor organ in the host.

After an organ has been transplanted into the patient, the patient's immune system is suppressed to prevent rejection of the new organ. Despite the wide use of immunosuppressive therapy, organ transplant rejection can occur.

Organ transplant rejection comprises three separate categories: hyperacute, acute and chronic. Hyperacute rejection is characterized by rapid thrombotic occlusion of the graft vasculature within minutes to hours after organ transplantation. Hyperacute rejection is mediated in large part by preexisting antibodies that bind to the epithelium and activate the complement cascade. Complement activation results in endothelial cell damage and subsequent exposure of the basement membrane, resulting in the activation of platelets, leading to thrombosis and vascular occlusion. As the field of transplantation has matured, hyperacute rejection has become less common due to blood antigen and MHC molecule matching between the donor organ and the recipient.

Acute rejection is sub-classified into acute vascular rejection and acute cellular rejection. Acute vascular rejection is characterized by necrosis of individual cells in the graft blood vessels. The process is similar to that of hyperacute rejection, but onset is often slower, within one week of rejection, and a T cell component may be involved. Acute vascular rejection is initiated by a response to alloantigens present on the vascular endothelial cells of the donor organ, resulting in the release of a cytokine cascade, inflammation, and eventual necrosis. Acute cellular rejection is often characterized by necrosis of the essential or parenchymal cells of the transplanted organ caused by the infiltration of host T lymphocytes and macrophages. The lymphocytes involved are usually cytotoxic T lymphocytes (CTL) and macrophages, both resulting in lysis of targeted cells. The CTLs are usually specific for graft alloantigens displayed in the context of MHC class I molecules.

Chronic rejection is the major cause of allograft loss and is characterized by fibrosis and loss of normal organ structures. Fibrosis may be the result of wound healing following the cellular necrosis of acute rejection, or may occur independently and without prior acute rejection. In addition, chronic rejection may lead to vascular occlusions thought to stem from a delayed type hypersensitivity response to alloantigens present on the transplanted organ. These alloantigens stimulate lymphocytes to secrete cytokines which attract macrophages and other effector cells eventually leading to an arteriosclerosis-like blockage.

In many cases, chronic graft injury or rejection (CR) is largely due to calcineurin-inhibitor drug nephrotoxicity (DT) and chronic allograft nephropathy (CAN), two conditions which may result in loss of graft function and early graft loss, premature to the life expectancy of the recipient. The incidence of chronic graft loss has remained unchanged over the last decade.

A biopsy is the only current gold standard for CAN and DT diagnosis. As both conditions are progressive post-transplantation, multiple graft protocol biopsies are required. However, the invasiveness of biopsy procedures is a limitation to this form of monitoring. In addition, variability of biopsy sampling and pathology analysis (2) adds a confounder to the differential diagnosis of these 2 conditions—the result of either too much drug (DT) vs. too little/inappropriate drugs (CAN)—with a common outcome of chronic fibrotic injury from differing mechanisms (non-immune vs. immune).

There is currently no method available to detect or to monitor future graft loss at the time of transplantation or acute rejection (AR) episodes. AR is a risk factor both for eventual graft loss, delayed recovery of graft function and even chronic rejection. Non-invasive monitoring methods for AR stratification, CR, DT and developing or established tolerance is currently not available, but would be very valuable, as the transplant biopsy, though the current gold standard, fails to stratify or prognosticate AR, differentiate CR clearly from DT or diagnose tolerance.

Accordingly, of interest would be the ability to evaluate likelihood of graft survival in a transplant recipient, e.g., following an AR episode, such that treatment protocols for transplant patients may be customized.

SUMMARY OF THE INVENTION

Methods are provided for evaluating a subject for graft survival, e.g., in terms of predicting graft survival, identifying the presence of a deleterious graft condition, such as CAN and DT, identifying the severity and class of acute rejection, etc, in a subject are provided. In practicing the subject methods, the expression of at least one gene in a sample from the subject, e.g., a blood or biopsy sample, is assayed, e.g., at the nucleic acid and/or protein level, to evaluate the subject. Also provided are compositions, systems and kits that find use in practicing the subject methods.

DEFINITIONS

For convenience, certain terms employed in the specification, examples, and appended claims are collected here.

"Acute rejection or AR" is the rejection by the immune system of a tissue transplant recipient when the transplanted tissue is immunologically foreign. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery. Generally, acute rejection can be inhibited or suppressed with immunosuppressive drugs such as rapamycin, cyclosporin A, anti-CD40L monoclonal antibody and the like.

"Chronic transplant rejection or CR" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs.

The term "transplant rejection" encompasses both acute and chronic transplant rejection.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1×SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

As used herein, the term "gene" or "recombinant gene" refers to a nucleic acid comprising an open reading frame encoding a polypeptide, including exon and (optionally) intron sequences. The term "intron" refers to a DNA sequence present in a given gene that is not translated into protein and is generally found between exons in a DNA molecule. In addition, a gene may optionally include its natural promoter (i.e., the promoter with which the exons and introns of the gene are operably linked in a non-recombinant cell, i.e., a naturally occurring cell), and associated regulatory sequences, and may or may not have sequences upstream of the AUG start site, and may or may not include untranslated leader sequences, signal sequences, downstream untranslated sequences, transcriptional start and stop sequences, polyadenylation signals, translational start and stop sequences, ribosome binding sites, and the like.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, procaryotic or eukaryotic mRNA, genomic DNA sequences from viral, procaryotic or eukaryotic DNA, and even synthetic DNA sequences. A transcription termination sequence may be located 3' to the coding sequence.

The terms "reference" and "control" are used interchangebly to refer to a known value or set of known values against which an observed value may be compared. As used herein, known means that the value represents an understood parameter, e.g., a level of expression of a marker gene in a graft survival or loss phenotype.

The term "nucleic acid" includes DNA, RNA (double-stranded or single stranded), analogs (e.g., PNA or LNA molecules) and derivatives thereof. The terms "ribonucleic acid" and "RNA" as used herein mean a polymer composed of ribonucleotides. The terms "deoxyribonucleic acid" and "DNA" as used herein mean a polymer composed of deoxyribonucleotides. The term "mRNA" means messenger RNA. An "oligonucleotide" generally refers to a nucleotide multimer of about 10 to 100 nucleotides in length, while a "polynucleotide" includes a nucleotide multimer having any number of nucleotides.

The terms "protein" and "polypeptide" used in this application are interchangeable. "Polypeptide" refers to a polymer of amino acids (amino acid sequence) and does not refer to a specific length of the molecule. Thus peptides and oligopeptides are included within the definition of polypeptide. This term does also refer to or include post-translational modifications of the polypeptide, for example, glycosylations, acetylations, phosphorylation and the like. Included within the definition are, for example, polypeptides containing one or more analogs of an amino acid, polypeptides with substituted linkages, as well as other modifications known in the art, both naturally occurring and non-naturally occurring.

The term "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

DESCRIPTION OF THE SPECIFIC EMBODIMENTS

Figure 1:
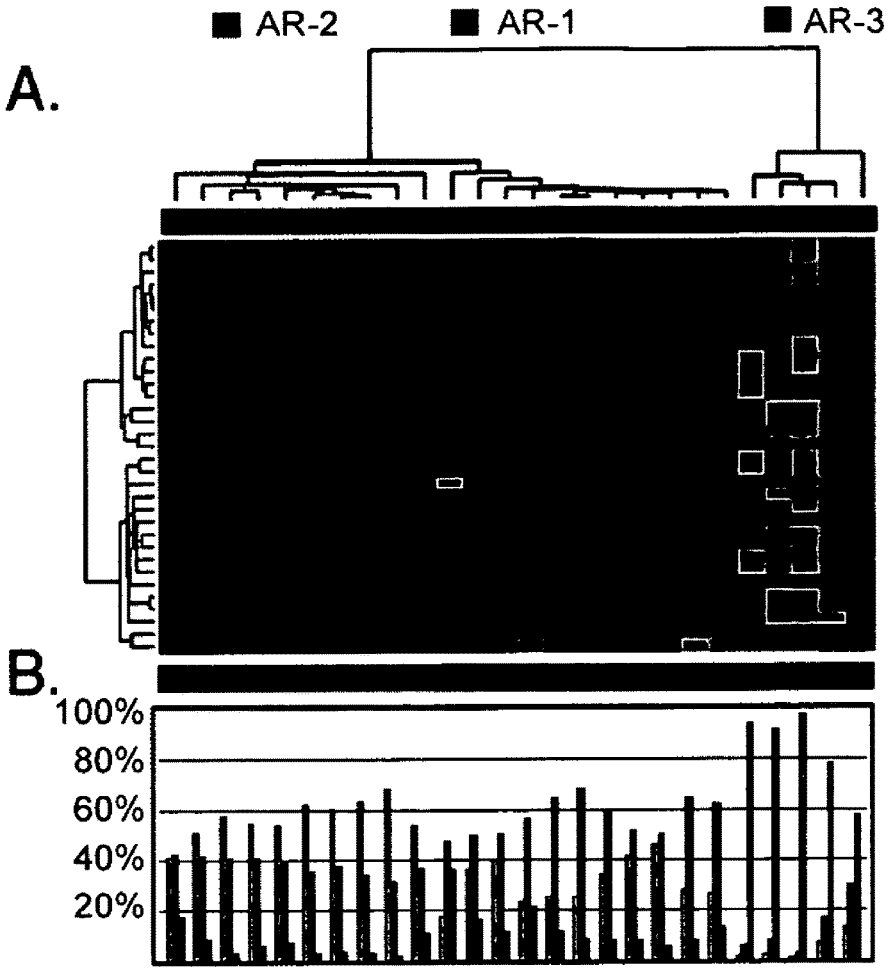
FIG. 1. Predictive Analysis of Microarrays (PAM) using a set of 3,170 differentially expressed genes identifies the 33 classifiers with similar power (FIG. 1A). The PAM classification scores grouped the samples with 100% concordance to assigned classes and reported scores are aligned with the clustered samples (FIG. 1B).

Methods are provided for evaluating a subject for graft function, e.g., in terms of predicting graft survival, identifying the presence of a deleterious graft condition, such as CAN and DT, identifying the severity and class of acute rejection, etc, in a subject are provided. In practicing the subject methods, the expression of at least one gene in a sample from the subject, e.g., a blood or biopsy sample, is assayed, e.g., at the nucleic acid and/or protein level, to evaluate the subject. Also provided are compositions, systems and kits that find use in practicing the subject methods. The methods and compositions find use in a variety of applications.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the subject invention is directed to methods of evaluating graft function in a subject, as well as reagents and kits for use in practicing the subject methods. In further describing the invention, the subject methods are described first, followed by a review of the reagents and kits for use in practicing the subject methods.

Methods of Evaluating Graft Function

As reviewed above, the subject invention provides methods for evaluating a subject for graft survival. The methods provide for evaluating a subject for graft survival in terms of a number of different factors. In certain embodiments, the factor evaluated is a basic prediction of graft survival. In certain embodiments, the factor evaluated is the presence of a deleterious graft condition, such as CAN and DT. In certain embodiments, the factor identified is the severity and/or class of acute rejection, where these embodiments are distinguished from methods that just identify the presence of acute rejection, since one is further determining the severity and/or class of acute rejection, and therefore an aspect of graft survival As such, certain embodiments of the invention provide methods of evaluating, e.g., in terms of predicting, graft survival in a subject comprising a graft. As such, the subject invention provides methods of evaluating whether a graft in a transplant patient or subject will survive or be lost. In certain embodiments, the methods may be viewed as methods of determining whether a transplant subject has a graft survival phenotype, i.e., a phenotype in which the graft will survive. A graft survival phenotype is a phenotype characterized by the presence of long-term graft survival. By "long-term" graft survival is meant graft survival for at least about 5 years beyond current sampling, despite the occurrence of one or more prior episodes of AR. In certain embodiments, graft survival is determined for patients in which at least one episode of acute rejection (AR) has occurred. As such, these embodiments are methods of determining or predicting graft survival following AR. Graft survival is determined or predicted in certain embodiments in the context of transplant therapy, e.g., immunosuppressive therapy, where immunosuppressive therapies are known in the art. In yet other embodiments, methods of distinguishing being organ rejection disease conditions, such as CAN and DT, are provided. In yet other embodiments, methods of determining the class and/or severity of acute rejection (and not just the presence thereof are provided.

As in known in the transplantation field, the graft organ, tissue or cell(s) may be allogeneic or xenogeneic, such that the grafts may be allografts or xenografts. Organs and tissues of interest include, but are not limited to: skin, heart, kidney, liver, bone marrow, and other organs.

In practicing the subject methods, a subject or patient sample, e.g., cells or collections thereof, e.g., tissues, is assayed to evaluate graft survival in the host, e.g., whether the graft will survive in the host from which the assayed sample was obtained. Accordingly, the first step of the subject methods is to obtain a suitable sample from the subject or patient of interest, i.e., a patient having at least one graft, e.g., allograft.

The sample is derived from any initial suitable source, where sample sources of interest include, but are not limited to, many different physiological sources, e.g., CSF, urine, saliva, tears, tissue derived samples, e.g., homogenates (such as biopsy samples of the transplanted tissue or organ (including, but not limited to kidney, heart, lung biopsies), and blood or derivatives thereof.

In certain embodiments, a suitable initial source for the patient sample is blood. As such, the sample employed in the subject assays of these embodiments is generally a blood-derived sample. The blood derived sample may be derived from whole blood or a fraction thereof, e.g., serum, plasma, etc., where in certain embodiments the sample is derived from blood cells harvested from whole blood. Of particular interest as a sample source are peripheral blood lymphocytes (PBL). Any convenient protocol for obtaining such samples may be employed, where suitable protocols are well known in the art and a representative protocol is reported in the Experimental Section, below.

In practicing the subject methods, the sample is assayed to obtain an expression evaluation, e.g., expression profile, for one or more genes, where the term expression profile is used broadly to include a genomic expression profile, e.g., an expression profile of nucleic acid transcripts, e.g., mRNAs, of the one or more genes of interest, or a proteomic expression profile, e.g., an expression profile of one or more different proteins, where the proteins/polypeptides are expression products of the one or more genes of interest. As such, in certain embodiments the expression of only one gene is evaluated. In yet other embodiments, the expression of two or more, e.g., about 5 or more, about 10 or more, about 15 or more, about 25 or more, about 50 or more, about 100 or more, about 200 or more, etc., genes is evaluated. Accordingly, in the subject methods, the expression of at least one gene in a sample is evaluated. In certain embodiments, the evaluation that is made may be viewed as an evaluation of the transcriptosome, as that term is employed in the art. See e.g., Gomes et al., Blood (2001 Jul. 1) 98(1): 93-9.

In generating the expression profile, in certain embodiments a sample is assayed to generate an expression profile that includes expression data for at least one gene/protein, usually a plurality of genes/proteins, where by plurality is meant at least two different genes/proteins, and often at least about 5, typically at least about 10 and more usually at least about 20 different genes/proteins or more, such as 50 or more, 100 or more, etc.

In the broadest sense, the expression evaluation may be qualitative or quantitative. As such, where detection is qualitative, the methods provide a reading or evaluation, e.g., assessment, of whether or not the target analyte, e.g., nucleic acid or expression product, is present in the sample being assayed. In yet other embodiments, the methods provide a quantitative detection of whether the target analyte is present in the sample being assayed, i.e., an evaluation or assessment of the actual amount or relative abundance of the target analyte, e.g., nucleic acid in the sample being assayed. In such embodiments, the quantitative detection may be absolute or, if the method is a method of detecting two or more different analytes, e.g., target nucleic acids, in a sample, relative. As such, the term "quantifying" when used in the context of quantifying a target analyte, e.g., nucleic acid(s), in a sample can refer to absolute or to relative quantification. Absolute quantification may be accomplished by inclusion of known concentration(s) of one or more control analytes and referencing the detected level of the target analyte with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other.

Genes/proteins of interest are graft survival/loss indicative genes, i.e., genes/proteins that are differentially expressed or present at different levels in graft survival and graft loss individuals (more specifically, individuals in which graft loss will occur vs. individuals in which a graft will survive). Representative genes/proteins of interest in certain embodiments include, but are not limited to, the genes/proteins provided in Tables 1 and 2. (Note that for Tables 1 and 2, the exact sequence of the clone identified in the table can be determined through the NCBI Entrez nucleotide database located at the website produced by placing "http://www." before: "ncbi.nlm.nih.gov/entrez/query.fcgi?CMD=search&db=nucleotide" in the navigation window of a web browser (e.g., Netscape); the sequence for a specific clone is then obtained by entering the clone ID in quotes as the search term).

TABLE 1

Genes of known function in whole blood predictive of graft loss following acute rejection

| Rank | Clone | Symbol | Gene | UnigeneID |
|---|---|---|---|---|
| 1 | IMAGE: 214006 | HIST1H2BC | Histone 1, H2bc | Hs.356901 |
| 2 | IMAGE: 826131 | IGHG3 | Ig heavy constant gamma 3 | Hs.413826 |
| 3 | IMAGE: 626318 | UBN1 | Ubinuclein 1 | Hs.21479 |
| 4 | IMAGE: 511387 | GLG1 | Golgi apparatus protein 1 | Hs.78979 |
| 5 | IMAGE: 810057 | CSDA | Cold shock domain protein A | Hs.221889 |
| 6 | IMAGE: 283919 | HIST1H2AC | Histone 1, H2ac | Hs.28777 |
| 7 | IMAGE: 453710 | PLEK2 | Pleckstrin 2 | Hs.170473 |
| 8 | IMAGE: 840821 | SSR4 | Signal sequence receptor, delta | Hs.409223 |
| 9 | IMAGE: 70201 | MSCP | Mitochondrial solute carrier | Hs.283716 |
| 10 | IMAGE: 66686 | RPL10 | Ribosomal protein L10 | Hs.77091 |
| 11 | IMAGE: 1306420 | AHSA2 | Activator of heat shock ATPase | Hs.122440 |
| 12 | IMAGE: 2578221 | UBB | Ubiquitin B | Hs.356190 |
| 13 | IMAGE: 811062 | CGI-69 | CGI-69 protein | Hs.237924 |
| 14 | IMAGE: 1272566 | TNFRSF10D | TNF receptor superfamily 10d | Hs.129844 |
| 15 | IMAGE: 1240649 | RPL10 | Ribosomal protein L10 | Hs.77091 |
| 16 | IMAGE: 85224 | RBM25 | RNA binding motif protein 25 | Hs.197184 |
| 17 | IMAGE: 2114004 | HIST1H3D | Histone 1, H3d | Hs.239458 |
| 18 | IMAGE: 789091 | HIST1H2AC | Histone 1, H2ac | Hs.28777 |
| 19 | IMAGE: 591025 | JMJD3 | Jumonji domain containing 3 | Hs.103915 |
| 20 | IMAGE: 1354406 | SSR4 | Signal sequence receptor, delta | Hs.409223 |
| 21 | IMAGE: 812276 | SNCA | Synuclein | Hs.76930 |
| 22 | IMAGE: 344720 | GYPC | Glycophorin C | Hs.81994 |
| 23 | IMAGE: 683899 | JMJD3 | Jumonji domain containing 3 | Hs.103915 |
| 24 | IMAGE: 825006 | CYorf15A | Chromosome Y ORF | Hs.171857 |
| 25 | IMAGE: 1492412 | UBA52 | Ubiquitin A-52 fusion product 1 | Hs.5308 |
| 26 | IMAGE: 854079 | ACTN1 | Actinin, alpha 1 | Hs.119000 |
| 27 | IMAGE: 366884 | IFNAR2 | Interferon (a- B- and o) receptor 2 | Hs.86958 |
| 28 | IMAGE: 812967 | TM4SF9 | Transmembrane 4 superfamily | Hs.8037 |
| 29 | IMAGE: 207794 | NFE2 | Erythroid nuclear factor | Hs.75643 |
| 30 | IMAGE: 359835 | SAT | Spermidine N1-acetyltransferase | Hs.28491 |
| 31 | IMAGE: 565849 | KLHL12 | Kelch-like 12 (*Drosophila*) | Hs.3826 |
| 32 | IMAGE: 256260 | RFC3 | Replication factor C activator | Hs.115474 |
| 33 | IMAGE: 191826 | MSCP | Mitochondrial solute carrier protein | Hs.283716 |
| 34 | IMAGE: 202242 | MIF | Macrophage migration inhibitor | Hs.407995 |
| 35 | IMAGE: 323506 | MAPK1 | Mitogen-activated protein kinase 1 | Hs.324473 |
| 36 | IMAGE: 1286850 | MME | Membrane metallo-endopeptidase | Hs.259047 |
| 37 | IMAGE: 129725 | RBPSUH | Recombining binding protein | Hs.347340 |
| 38 | IMAGE: 882522 | ASS | Argininosuccinate synthetase | Hs.160786 |
| 39 | IMAGE: 2129439 | UBE2B | Ubiquitin-conjugating enzyme E2B | Hs.385986 |
| 40 | IMAGE: 1687138 | HIST1H2AM | Histone 1, H2am | Hs.134999 |
| 41 | IMAGE: 209655 | TGFBR3 | TGFb receptor III | Hs.342874 |
| 42 | IMAGE: 75254 | CSRP2 | Cysteine and glycine-rich protein 2 | Hs.10526 |
| 43 | IMAGE: 1715851 | HBG2 | Hemoglobin, gamma G | Hs.302145 |
| 44 | IMAGE: 155467 | SLC9A3R2 | Solute carrier family 9 | Hs.440896 |
| 45 | IMAGE: 561743 | PPP1R1A | Protein phosphatase 1 | Hs.435238 |
| 46 | IMAGE: 565075 | STC1 | Stanniocalcin 1 | Hs.25590 |
| 47 | IMAGE: 1541958 | POU2AF1 | POU domain associating factor | Hs.2407 |
| 48 | IMAGE: 324122 | ESM1 | Endothelial cell-specific molecule 1 | Hs.129944 |
| 49 | IMAGE: 80338 | SELENBP1 | Selenium binding protein 1 | Hs.334841 |
| 50 | IMAGE: 1472754 | COX6B1 | Cytochrome c oxidase (ubiquitous) | Hs.431668 |
| 51 | IMAGE: 233583 | IL1R2 | Interleukin 1 receptor, type II | Hs.25333 |
| 52 | IMAGE: 490060 | RNF159 | Ring finger protein (C3HC4 type) | Hs.246914 |
| 53 | IMAGE: 1185475 | ABCC5 | ATP-binding cassette C | Hs.22010 |
| 54 | IMAGE: 120551 | LPIN2 | Lipin 2 | Hs.437425 |
| 55 | IMAGE: 162772 | EGR1 | Early growth response 1 | Hs.326035 |
| 56 | IMAGE: 322029 | MAPK9 | Mitogen-activated protein kinase 9 | Hs.348446 |
| 57 | IMAGE: 1305158 | KIAA1219 | KIAA1219 protein | Hs.348929 |
| 58 | IMAGE: 2505604 | SCYE1 | Endothelial monocyte-activating) | Hs.105656 |
| 59 | IMAGE: 1240813 | IGKC | Immunoglobulin kappa constant | Hs.377975 |
| 60 | IMAGE: 257637 | RRBP1 | Ribosome binding protein 1 homolog | Hs.98614 |
| 61 | IMAGE: 381522 | PP1057 | Hypothetical protein PP1057 | Hs.108557 |
| 62 | IMAGE: 455123 | MTSS1 | Metastasis suppressor 1 | Hs.77694 |

TABLE 2

Genes of known function in renal biopsies whole blood predictive of graft loss following acute rejection.

| Rank | Clone | Symbol | Gene | Unigene ID |
|---|---|---|---|---|
| 1 | IMAGE: 2134209 | ZNF41 | Zinc finger protein 41 | Hs.143700 |
| 2 | IMAGE: 1241524 | TCL1A | T-cell leukemia/lymphoma 1A | Hs.2484 |
| 3 | IMAGE: 704915 | TAP1 | Transporter 1 (MDR/TAP) | Hs.352018 |
| 4 | IMAGE: 267600 | STAT6 | Interleukin-4 induced STAT6 | Hs.437475 |
| 5 | IMAGE: 26599 | STAT1 | Interleukin-4 induced STAT1 | Hs.21486 |
| 6 | IMAGE: 210405 | PSME2 | Proteasome activator | Hs.434081 |
| 7 | IMAGE: 1240661 | PSMB9 | Proteasome beta type, 9 | Hs.381081 |
| 8 | IMAGE: 705046 | PML | Promyelocytic leukemia | Hs.89633 |
| 9 | IMAGE: 824340 | NCF1 | Neutrophil cytosolic factor 1 | Hs.1583 |
| 10 | IMAGE: 753313 | LAPTM5 | Lysosomal-associated protein-5 | Hs.436200 |
| 11 | IMAGE: 1351990 | ISG20 | Interferon stimulated gene 20 kDa | Hs.105434 |
| 12 | IMAGE: 1672498 | IGLV@ | Ig lambda variable group | Hs.449601 |
| 13 | IMAGE: 1240590 | IGLC2 | Ig lambda constant 2 | Hs.405944 |
| 14 | IMAGE: 1240813 | IGKC | Ig kappa constant | Hs.377975 |
| 15 | IMAGE: 1604703 | HLA-F | MHC complex, class I, F | Hs.411958 |
| 16 | IMAGE: 2448698 | HLA-DRB6 | MHC, class II, DR beta 6 (pseudogene) | Hs.534338 |
| 17 | IMAGE: 461769 | HLA-DRB5 | MHC complex, class II, DR beta 5 | Hs.308026 |
| 18 | IMAGE: 1241341 | HLA-DRB3 | MHC complex, class II, DR beta 3 | Hs.520049 |
| 19 | IMAGE: 1241211 | HLA-DPB1 | MHC complex, class II, DP beta 1 | Hs.368409 |
| 20 | IMAGE: 203527 | HLA-A | MHC complex, class I, A | Hs.181244 |
| 21 | IMAGE: 853906 | HCG4P6 | HLA complex group 4 pseudogene 6 | Hs.512759 |
| 22 | IMAGE: 841008 | GBP1 | Guanylate binding 1, interferon-inducible | Hs.62661 |
| 23 | IMAGE: 277522 | DAF | Decay accelerating factor complement (CD55) | Hs.408864 |
| 24 | IMAGE: 269295 | CD83 | CD83 antigen (Activated B lymphocytes) | Hs.444310 |
| 25 | IMAGE: 276727 | CD69 | CD69 antigen (early T-cell activation antigen) | Hs.82401 |
| 26 | IMAGE: 200720 | CD38 | CD38 antigen (p45) | Hs.174944 |
| 27 | IMAGE: 2000918 | CAS1 | O-acetyltransferase | Hs.324725 |
| 28 | IMAGE: 67042 | APOM | Apolipoprotein M | Hs.247323 |
| 29 | IMAGE: 488143 | IGHM | Immunoglobulin heavy locus | Hs.103995 |
| 30 | IMAGE: 207718 | | TASS Ig light chain variable region | Hs.449578 |

In certain embodiments, at least one of the genes/proteins in the prepared expression profile is a graft survival/rejection indicative gene from Tables 1 and/or 2, where the expression profile may include expression data for 5, 10, 20, 50, 75 or more of, including all of, the genes/proteins listed in Tables 1 and/or 2. The number of different genes/proteins whose expression and/or quantity data, i.e., presence or absence of expression, as well as expression/quantity level, that are included in the expression profile that is generated may vary, but may be at least 2, and in certain embodiments ranges from 2 to about 100 or more, sometimes from 3 to about 75 or more, including from about 4 to about 70 or more.

In certain embodiments, additional genes beyond those listed in Tables 1 and/or 2, may be assayed, such as genes whose expression pattern can be used to evaluate additional transplant characteristics, including but not limited to: acute rejection (e.g., the genes identified as AR in Table 3, below); chronic allograft injury (chronic rejection) in blood (e.g., the genes identified as CR in Table 3, below); immunosuppressive drug toxicity or adverse side effects including drug-induced hypertension (e.g., the genes identified as DT in Table 3, below); age or body mass index associated genes that correlate with renal pathology or account for differences in recipient age-related graft acceptance (e.g., the genes identified as BMI in Table 3, below); immune tolerance markers in whole blood (e.g., the genes identified as TOL in Table 3, below); genes found in literature surveys with immune modulatory roles that may play a role in transplant outcomes (e.g., the genes identified as Lit. in Table 3, below); as well as other array assay function related genes, e.g., for assessing sample quality (3'- to 5'-bias in probe location), sampling error in biopsy-based studies, cell surface markers, and normalizing genes for calibrating hybridization results (see e.g., the genes identified as Contr. in Table 3, below); and the like.

A representative collection of genes that includes not only graft survival/rejection genes of Tables 1 and 2 above, but also additional graft characterizing genes (e.g., specific for DT, CAN, and immune tolerance) is in Table 3.

TABLE 3

Genes of known function of prognostic value compiled for a custom transplantation chip (TxChip VI).

| Symbol | Name | mRNA | Tissue | Study |
|---|---|---|---|---|
| ACOX1 | Acyl-Coenzyme A oxidase 1, palmitoyl | NM_004035 | Blood | AR |
| ADD3 | Adducin 3 (gamma) | NM_016824 | Blood | AR |
| ADM | Adrenomedullin | NM_001124 | Blood | AR |
| AHR | Aryl hydrocarbon receptor | NM_001621 | Blood | AR |
| ATP1A1 | ATPase, Na+/K+ transporting, alpha 1 | NM_000701 | Blood | AR |
| BUB1B | BUB1 budding uninhibited by benzimidazoles | NM_001211 | Blood | AR |
| CASP8 | Caspase 8, apoptosis-related cysteine protease | NM_001228 | Blood | AR |
| CASP8AP2 | CASP8 associated protein 2 | NM_012115 | Blood | AR |

TABLE 3-continued

Genes of known function of prognostic value compiled for a custom transplantation chip (TxChip VI).

| Symbol | Name | mRNA | Tissue | Study |
|---|---|---|---|---|
| CCNC | Cyclin C | NM_005190 | Blood | AR |
| CD21 | CD21 B-cell receptor for complement C3d0 | Y00649 | Blood | AR |
| CD69 | CD69 antigen (early T-cell activation antigen) | NM_001781 | Blood | AR |
| CD8A | CD8 antigen, alpha polypeptide (p32) | NM_001768 | Blood | AR |
| CDIPT | Phosphatidylinositol synthase | NM_145752 | Blood | AR |
| COX6C | Cytochrome c oxidase subunit VIc | NM_004374 | Blood | AR |
| CSNK1A1 | Casein kinase 1, alpha 1 | NM_001892 | Blood | AR |
| DUSP1 | Dual specificity phosphatase 1 | NM_004417 | Blood | AR |
| DUSP3 | Dual specificity phosphatase 3 | NM_004090 | Blood | AR |
| EIF1A | Eukaryotic translation initiation factor 1A | NM_001412 | Blood | AR |
| EIF2S3 | Eukaryotic translation initiation factor 2 | NM_001415 | Blood | AR |
| GNLY | Granulysin | NM_006433 | Blood | AR |
| GOLGIN-67 | Golgin-67 | XM_496064 | Blood | AR |
| AHSA2 | Activator of heat shock ATPase | NM_152392 | Blood | AR |
| HIST1H2BC | Histone 1, H2bc | NM_003526 | Blood | AR |
| IFNAR2 | Interferon (alpha, beta and omega) receptor 2 | NM_000874 | Blood | AR |
| IGHG1 | Ig heavy constant gamma 1 (G1m marker) | AB067073 | Blood | AR |
| IL1R2 | Interleukin 1 receptor, type II | NM_004633 | Blood | AR |
| MAPK1 | Mitogen-activated protein kinase 1 | NM_002745 | Blood | AR |
| MIF | Macrophage migration inhibitory factor | NM_002415 | Blood | AR |
| SCYE1 | Endothelial monocyte-activating | NM_004757 | Blood | AR |
| TGFBR3 | TGFb receptor III (betaglycan) | NM_003243 | Blood | AR |
| TM4SF9 | Transmembrane 4 superfamily member 9 | NM_005723 | Blood | AR |
| IGHM | Immunoglobulin heavy constant mu | X58529 | Blood | AR |
| ISG20 | Interferon stimulated gene 20 kDa | NM_002201 | Blood | AR |
| KIAA1014 | FNBP4 formin binding protein 4 | AB023231 | Blood | AR |
| LIV-1 | SLC39A6 metal ion transporter | NM_015359 | Blood | AR |
| MAPKAPK5 | Mitogen-activated protein kinase | NM_003668 | Blood | AR |
| MDM4 | p53 binding protein | NM_002393 | Blood | AR |
| MYT1 | Myelin transcription factor 1 | NM_004535 | Blood | AR |
| NAB1 | EGR1 binding protein 1 | NM_005966 | Blood | AR |
| NFKB1 | NFkB enhancer in B-cells 1 (p105) | NM_003998 | Blood | AR |
| PC4 | RNA polymerase II transcription cofactor 4 | NM_006713 | Blood | AR |
| PKM2 | Pyruvate kinase, muscle | NM_002654 | Blood | AR |
| PTP4A1 | Protein tyrosine phosphatase | NM_003463 | Blood | AR |
| RBL2 | Retinoblastoma-like 2 (p130) | NM_005611 | Blood | AR |
| RBM3 | RNA binding motif 3 (RNP1, RRM) | NM_006743 | Blood | AR |
| REL | V-rel viral oncogene homolog | NM_002908 | Blood | AR |
| RPL22 | Ribosomal protein L22 | NM_000983 | Blood | AR |
| RPS24 | Ribosomal protein S24 | NM_033022 | Blood | AR |
| RPS27 | Ribosomal protein S27 | NM_001030 | Blood | AR |
| RPS4Y | RPS4Y ribosomal protein S4 | NM_001008 | Blood | AR |
| SATB1 | Special AT-rich sequence binding protein | NM_002971 | Blood | AR |
| SDS3 | Likely ortholog of mouse Sds3 | NM_022491 | Blood | AR |
| SSBP1 | Single-stranded DNA binding protein 1 | NM_003143 | Blood | AR |
| SSI-3 | SOCS3 suppressor of cytokine signaling 3 | NM_003955 | Blood | AR |
| STK4 | Serine/threonine kinase 4 | NM_006282 | Blood | AR |
| TBRG1 | Transforming growth factor beta regulator 1 | NM_032811 | Blood | AR |
| TCF7 | Transcription factor 7 (T-cell specific) | NM_201633 | Blood | AR |
| TOP2B | Topoisomerase (DNA) II beta 180 kDa | NM_001068 | Blood | AR |
| TRIM | T-cell receptor interacting molecule | NM_016388 | Blood | AR |
| TRRAP | Transcription domain-associated protein | NM_003496 | Blood | AR |
| UBA52 | Ubiquitin A-52-ribosomal protein fusion | NM_003333 | Blood | AR |
| UBB | Ubiquitin B | NM_018955 | Blood | AR |
| UBE2B | Ubiquitin-conjugating enzyme E2B | NM_003337 | Blood | AR |
| UBN1 | Ubinuclein 1 | NM_016936 | Blood | AR |
| USP25 | Ubiquitin specific protease 25 | NM_013396 | Blood | AR |
| AIM1 | Absent in melanoma 1 | XM_166300 | Biopsy | AR |
| CD38 | CD38 antigen (p45) | NM_001775 | Biopsy | AR |
| CDS1 | CDP-diacylglycerol synthase | NM_001263 | Biopsy | AR |
| CSF1R | Feline sarcoma viral (v-fms) homolog | NM_005211 | Biopsy | AR |
| DR1 | Down-regulator of transcription 1 | NM_001938 | Biopsy | AR |
| FGL2 | Fibrinogen-like 2 | NM_006682 | Biopsy | AR |
| FLJ13612 | Calcium binding protein | AI635773 | Biopsy | AR |
| HLA-A | MHC class I, A | NM_002116 | Biopsy | AR |
| HLA-B | MHC class I, B | NM_005514 | Biopsy | AR |
| HLA-C | MHC class I, C | NM_002117 | Biopsy | AR |
| HLA-DPA1 | MHC class II, DP alpha 1 | NM_033554 | Biopsy | AR |
| HLA-DRA | MHC class II, DR alpha | NM_019111 | Biopsy | AR |
| IGKC | Ig kappa constant | AB064140 | Blood | AR |
| TNFSF10 | TNF superfamily, member 10 | NM_003810 | Blood | AR |
| IGLJ3 | IGLa Immunoglobulin lambda | AI146764 | Biopsy | AR |
| MYH10 | Myosin, heavy polypeptide 10 | NM_005964 | Biopsy | AR |
| NKTR | Natural killer-tumor recognition sequence | NM_005385 | Biopsy | AR |
| PAX8 | Paired box gene 8 | NM_013951 | Biopsy | AR |

TABLE 3-continued

Genes of known function of prognostic value compiled for a custom transplantation chip (TxChip VI).

| Symbol | Name | mRNA | Tissue | Study |
|---|---|---|---|---|
| POLR2B | Polymerase (RNA) II polypeptide B | NM_000938 | Biopsy | AR |
| RGN | Regucalcin (senescence marker protein-30) | NM_004683 | Biopsy | AR |
| SCNN1A | Sodium channel, nonvoltage-gated 1 alpha | NM_001038 | Biopsy | AR |
| SIM2 | Single-minded homolog 2 | NM_009586 | Biopsy | AR |
| TACSTD2 | Calcium signal transducer 2 | NM_002353 | Biopsy | AR |
| VCAM1 | Vascular cell adhesion molecule 1 | NM_001078 | Biopsy | AR |
| YARS | Tyrosyl-tRNA synthetase | NM_003680 | Biopsy | AR |
| ZFP36L1 | Zinc finger protein 36 | NM_004926 | Biopsy | AR |
| HLA-DPB1 | MHC, class II, DP beta 1 | NM_002121 | Biopsy | AR |
| HLA-DRB3 | MHC, class II, DR beta 4 | NM_022555 | Biopsy | AR |
| ACK1 | Cdc42-associated kinase 1 | NM_005781 | Biopsy | AR |
| HLA-F | MHC, class I, F | NM_018950 | Biopsy | AR |
| ICAM5 | Intercellular adhesion molecule 5 | NM_003259 | Biopsy | AR |
| REG1A | Regenerating islet-derived 1 alpha | NM_002909 | Biopsy | AR |
| GSTA2 | Glutathione S-transferase A2 | NM_000846 | Biopsy | AR |
| HLA-DRB5 | MHC class II, DR beta 4 | NM_002125 | Biopsy | AR |
| HLA-DQA1 | MHC class II, DQ alpha 1 | NM_002122 | Biopsy | AR |
| HLA-DQB1 | MHC class II, DQ beta 1 | NM_002123 | Biopsy | AR |
| RFXANK | Regulatory factor X-associated ankyrin | NM_003721 | Biopsy | AR |
| STAT6 | Interleukin-4 induced STAT6 | NM_003153 | Biopsy | AR |
| TAP1 | Transporter 1 (MDR/TAP) | NM_000593 | Biopsy | AR |
| DAF | Decay accelerating factor (CD55) | NM_000574 | Biopsy | AR |
| CD83 | CD83 antigen (activated B lymphocytes) | NM_004233 | Biopsy | AR |
| STAT1 | Interleukin-4 induced STAT1 | NM_007315 | Biopsy | AR |
| LTBR | Lymphotoxin beta receptor | NM_002342 | Biopsy | AR |
| KCNJ1 | Potassium inwardly-rectifying channel | NM_000220 | Biopsy | AR |
| SLPI | Secretory leukocyte protease inhibitor | NM_003064 | Biopsy | AR |
| CD34 | CD34 antigen | NM_001773 | Biopsy | AR |
| HOXB5 | Homeo box B5 | NM_002147 | Biopsy | AR |
| IL6R | Interleukin 6 receptor | NM_181359 | Biopsy | AR |
| DAPK1 | Death-associated protein kinase 1 | NM_004938 | Biopsy | AR |
| HOXD9 | Homeo box D9 | NM_014213 | Biopsy | AR |
| TCF21 | Transcription factor 21 | NM_003206 | Biopsy | AR |
| MAL | T-cell differentiation protein | NM_022438 | Biopsy | AR |
| MAF | V-maf fibrosarcoma homolog | NM_005360 | Blood | AR |
| NCOR2 | Nuclear receptor co-repressor 2 | NM_006312 | Blood | CR |
| ZFP106 | Zinc finger protein 106 homolog | NM_022473 | Blood | CR |
| RPL23 | Ribosomal protein L23 | NM_000978 | Blood | CR |
| CPVL | Carboxypeptidase, vitellogenic-like | NM_019029 | Blood | CR |
| ENO2 | Enolase 2 (gamma, neuronal) | NM_001975 | Blood | CR |
| CAPN2 | Calpain 2, (m/II) large subunit | NM_001748 | Blood | CR |
| FGFR4 | Fibroblast growth factor receptor 4 | NM_002011 | Blood | CR |
| CD68 | CD68 antigen | NM_001251 | Blood | CR |
| HK3 | Hexokinase 3 (white cell) | NM_002115 | Blood | CR |
| DUSP6 | Dual specificity phosphatase 6 | NM_001946 | Blood | CR |
| IL6ST | Interleukin 6 signal transducer | NM_002184 | Blood | CR |
| LATS2 | LATS, large tumor suppressor 2 | NM_014572 | Blood | CR |
| MIC2 | CD99 antigen | NM_002414 | Blood | CR |
| MMP23B | Matrix metalloproteinase 23B | NM_006983 | Blood | CR |
| ZNF511 | Zinc finger protein 511 | NM_145806 | Blood | CR |
| ANXA5 | Annexin A5 | NM_001154 | Blood | CR |
| ID2 | Inhibitor of DNA binding 2 | NM_002166 | Blood | CR |
| PRKRIR | RNA dependent p58 repressor | NM_004705 | Blood | CR |
| SGK | Serum/glucocorticoid regulated kinase | NM_005627 | Blood | CR |
| S100A10 | S100 calcium binding protein A10 | NM_002966 | Blood | CR |
| CYP51 | Cytochrome P450, family 51A | NM_000786 | Blood | CR |
| ITGA4 | Integrin, alpha 4 (antigen CD49D) | NM_000885 | Blood | CR |
| ADAM10 | A disintegrin and metalloproteinase10 | NM_001110 | Blood | CR |
| HNRPK | Nuclear ribonucleoprotein K | NM_031262 | Blood | CR |
| ITGAV | Integrin, alpha V (CD51) | NM_002210 | Blood | CR |
| JUN | V-jun sarcoma virus 17 homolog | NM_002228 | Blood | CR |
| PRKAR2B | Protein kinase regulator | NM_002736 | Blood | CR |
| TIE | Tyrosine kinase with Ig and EGF domains | NM_005424 | Blood | CR |
| IQGAP2 | GTPase activating protein 2 | NM_006633 | Blood | CR |
| MAP4K1 | Mitogen-activated protein kinase 1 | NM_007181 | Blood | CR |
| ILF3 | Interleukin enhancer binding factor 3 | NM_012218 | Blood | CR |
| SGKL | Serum/glucocorticoid regulated kinase-like | NM_013257 | Blood | CR |
| GLS | Glutaminase | NM_014905 | Blood | CR |
| DPYD | Dihydropyrimidine dehydrogenase | NM_000110 | Blood | CR |
| ACADM | Acyl-Coenzyme A dehydrogenase | NM_000016 | Biopsy | DT |
| AUTS2 | Autism susceptibility candidate 2 | NM_015570 | Biopsy | DT |
| CA2 | Carbonic anhydrase II | NM_000067 | Biopsy | DT |
| CTNNA1 | Catenin (cadherin-associated protein) | NM_001903 | Biopsy | DT |
| CXCL12 | Stromal cell-derived factor 1 | NM_000609 | Biopsy | DT |
| DDR1 | Discoidin domain receptor family, member 1 | NM_013994 | Biopsy | DT |

TABLE 3-continued

Genes of known function of prognostic value compiled for a custom transplantation chip (TxChip VI).

| Symbol | Name | mRNA | Tissue | Study |
|---|---|---|---|---|
| DECR1 | 2,4-dienoyl CoA reductase 1, mitochondrial | NM_001359 | Biopsy | DT |
| DEDD | Death effector domain containing | NM_032998 | Biopsy | DT |
| DPP4 | Dipeptidylpeptidase 4 (CD26) | NM_001935 | Biopsy | DT |
| ITM2B | Integral membrane protein 2B | NM_021999 | Biopsy | DT |
| KIAA0436 | L-type neutral amino acid transporter | AB007896 | Biopsy | DT |
| LDHB | Lactate dehydrogenase B | NM_002300 | Biopsy | DT |
| LEPR | Leptin receptor | NM_002303 | Biopsy | DT |
| LRBA | LPS-responsive vesicle trafficking | NM_006726 | Biopsy | DT |
| MUT | Methylmalonyl Coenzyme A mutase | NM_000255 | Biopsy | DT |
| NAT1 | N-acetyltransferase 1 | NM_000662 | Biopsy | DT |
| NAT2 | N-acetyltransferase 2 | NM_000015 | Biopsy | DT |
| NUP50 | Nucleoporin 50 kDa | NM_153645 | Biopsy | DT |
| PAFAH1B1 | Platelet-activating factor | NM_000430 | Biopsy | DT |
| PDZK3 | PDZ domain containing 3 | NM_178140 | Biopsy | DT |
| PLCL2 | Phospholipase C-like 2 | NM_015184 | Biopsy | DT |
| PPP2CB | Protein phosphatase 2 | NM_004156 | Biopsy | DT |
| PRKCM | Protein kinase C, mu | NM_002742 | Biopsy | DT |
| PTPN3 | Protein tyrosine phosphatase | NM_002829 | Biopsy | DT |
| REST | RE1-silencing transcription factor | NM_005612 | Biopsy | DT |
| SGCB | Sarcoglycan, beta | NM_000232 | Biopsy | DT |
| SHB | Src homology 2 domain containing | NM_003028 | Biopsy | DT |
| SORL1 | Sortilin-related receptor, L | NM_003105 | Biopsy | DT |
| SULT1E1 | Sulfotransferase family 1E | NM_005420 | Biopsy | DT |
| CBL | Cas-Br-Transforming sequence | NM_005188 | Biopsy | DT |
| CXCL1 | Chemokine (C—X—C motif) ligand 1 | NM_001511 | Biopsy | DT |
| FGF2 | Fibroblast growth factor 2 (basic) | NM_002006 | Biopsy | DT |
| GPRK5 | G protein-coupled receptor kinase 5 | NM_005308 | Biopsy | DT |
| ITSN2 | Intersectin 2 | NM_006277 | Biopsy | DT |
| BCL2L13 | BCL2-like 13 (apoptosis facilitator) | AA279535 | Biopsy | BMI |
| BDKRB2 | Bradykinin receptor B2 | NM_000623 | Biopsy | BMI |
| DDX3 | DEAD/H (Asp-Glu-Ala-Asp/His) box 3 | NM_001356 | Biopsy | BMI |
| FOXM1 | Forkhead box M1 | NM_021953 | Biopsy | BMI |
| HMOX2 | Heme oxygenase (decycling) 2 | NM_002134 | Biopsy | BMI |
| IFNGR1 | Interferon gamma receptor 1 | NM_000416 | Biopsy | BMI |
| IGFBP1 | Insulin-like growth factor binding protein 1 | NM_000596 | Biopsy | BMI |
| IGFBP5 | Insulin-like growth factor binding protein 5 | NM_000599 | Biopsy | BMI |
| LRP2 | Low density lipoprotein-related protein 2 | NM_004525 | Biopsy | BMI |
| MCM7 | Minichromosome maintenance deficient 7 | NM_182776 | Biopsy | BMI |
| NPPB | Natriuretic peptide precursor B | NM_002521 | Biopsy | BMI |
| NPR1 | Natriuretic peptide receptor A | NM_000906 | Biopsy | BMI |
| PAXIP1L | PAX transcription activation interacting | NM_007349 | Biopsy | BMI |
| PDCD5 | Programmed cell death 5 | NM_004708 | Biopsy | BMI |
| RBX1 | Ring-box 1 | NM_014248 | Biopsy | BMI |
| RPL27 | Ribosomal protein L27 | NM_000988 | Biopsy | BMI |
| SBA2 | WD repeat and SOCS box containing protein | AA043793 | Biopsy | BMI |
| SERPINB6 | Proteinase inhibitor, clade B (ovalbumin) | NM_004568 | Biopsy | BMI |
| SLC22A5 | Solute carrier family 22 | NM_003060 | Biopsy | BMI |
| SLC38A2 | Solute carrier family 38, member 2 | NM_018976 | Biopsy | BMI |
| SMT3H2 | Suppressor of MIF | NM_006937 | Biopsy | BMI |
| TJP4 | Tight junction protein 4 (peripheral) | NM_080604 | Biopsy | BMI |
| TP53INP1 | p53 inducible nuclear protein 1 | NM_033285 | Biopsy | BMI |
| BHLHB2 | Basic helix-loop-helix domain containing | NM_003670 | Biopsy | BMI |
| CSPG2 | Chondroitin sulfate proteoglycan 2 | NM_004385 | Biopsy | BMI |
| GPD1 | Glycerol-3-phosphate dehydrogenase 1 | NM_005276 | Biopsy | BMI |
| GTPBP4 | GTP binding 4; Chronic renal failure gene | NM_012341 | Biopsy | BMI |
| HIF1A | Hypoxia-inducible factor 1, alpha | NM_001530 | Biopsy | BMI |
| MMP7 | Matrix metalloproteinase 7 | NM_002423 | Biopsy | BMI |
| SLC2A3 | Facilitated glucose transporter | NM_006931 | Biopsy | BMI |
| THBS1 | Thrombospondin 1 | NM_003246 | Biopsy | BMI |
| TNC | Tenascin C (hexabrachion) | NM_002160 | Biopsy | BMI |
| HLA-G | HLA-G histocompatibility antigen, class I, G | NM_002127 | Blood | TOL |
| IGHG3 | Ig heavy constant gamma 3 | AK097306 | Blood | TOL |
| BUR1 | Budding uninhibited (cell cycle regulator) | NM_004336 | Blood | TOL |
| CCNB2 | Cyclin B2 | NM_004701 | Blood | TOL |
| TACSTD1 | Tumor-associated calcium signaling | NM_002354 | Blood | TOL |
| DHRS2 | Dehydrogenase/reductase (SDR family) | AK092834 | Blood | TOL |
| BMP7 | Bone morphogenetic protein 7 | NM_001719 | Blood | TOL |
| AKR1C1 | Aldo-keto reductase family 1C1 | NM_001353 | Blood | TOL |
| B4GALT2 | UDP-Gal 1,4-galactosyltransferase | NM_003780 | Blood | TOL |
| TCEB3 | Transcription elongation factor B (SIII) | NM_003198 | Blood | TOL |
| MLPH | Melanophilin | NM_024101 | Blood | TOL |
| SERPINH2 | Heat shock protein 47 (proteinase inhibitor) | NM_001235 | Blood | TOL |
| RRM2 | Ribonucleotide reductase M2 polypeptide | NM_001034 | Blood | TOL |
| SERPINA3 | Alpha-1 antiproteinase, antitrypsin | NM_001085 | Blood | TOL |
| SERPINA5 | Alpha-1 antiproteinase, antitrypsin | NM_000624 | Blood | TOL |

TABLE 3-continued

Genes of known function of prognostic value compiled for a custom transplantation chip (TxChip VI).

| Symbol | Name | mRNA | Tissue | Study |
|---|---|---|---|---|
| CTNNAL1 | Catenin (cadherin-associated protein) | NM_003798 | Blood | TOL |
| SPARC | Secreted protein, cysteine-rich (osteonectin) | NM_003118 | Blood | TOL |
| C1S | C1S complement component 1 | NM_001734 | Blood | TOL |
| SRPUL | SRPUL sushi-repeat protein | NM_006307 | Blood | TOL |
| MMP2 | Matrix metalloproteinase 2 | NM_004530 | Blood | TOL |
| SLC7A7 | Cationic amino acid transporter | NM_003982 | Blood | TOL |
| EPOR | Erythropoietin receptor | NM_000121 | Blood | TOL |
| PRAME | Preferentially expressed antigen in melanoma | NM_006115 | Blood | TOL |
| AFP | Alpha-fetoprotein | NM_001134 | Blood | TOL |
| MAPK9 | Mitogen-activated protein kinase 9 | NM_002752 | Blood | TOL |
| NR2F2 | Nuclear receptor subfamily 2F2 | NM_021005 | Blood | TOL |
| PFN2 | Profilin 2 | NM_053024 | Blood | TOL |
| SLC38A6 | Solute carrier family 38, member 6 | BC050349 | Blood | TOL |
| MYOM2 | Myomesin (M-protein) 2, 165 kDa | NM_003970 | Blood | TOL |
| RBP1 | Retinol binding protein 1, cellular | NM_002899 | Blood | TOL |
| TK1 | Thymidine kinase 1, soluble | NM_003258 | Blood | TOL |
| IFITM3 | Interferon induced transmembrane protein 3 | NM_021034 | Blood | TOL |
| APOH | Apolipoprotein H (beta-2-glycoprotein I) | NM_000042 | Blood | TOL |
| EVI2A | Ecotropic viral integration site 2A | NM_014210 | Blood | TOL |
| CD9 | CD9 antigen (p24) | NM_001769 | Blood | TOL |
| NKG7 | Natural killer cell group 7 sequence | NM_005601 | Blood | TOL |
| CDKN3 | Cyclin-dependent kinase inhibitor 3 | NM_005192 | Blood | TOL |
| TCL1A | T-cell leukemia/lymphoma 1A | NM_021966 | Blood | TOL |
| PYCR1 | Pyrroline-5-carboxylate reductase 1 | NM_153824 | Blood | TOL |
| TM4SF5 | Transmembrane 4 superfamily member 5 | NM_003963 | Blood | TOL |
| GAGEB1 | G antigen, family B, 1 (prostate associated) | NM_003785 | Blood | TOL |
| PCP4 | Purkinje cell protein 4 | NM_006198 | Blood | TOL |
| LGMN | Legumain | NM_005606 | Blood | TOL |
| PIR | Pirin (iron-binding nuclear protein) | NM_178238 | Blood | TOL |
| PAICS | Phosphoribosylaminoimidazole carboxylase | NM_006452 | Blood | TOL |
| IGFBP3 | Insulin-like growth factor binding protein 3 | NM_000598 | Blood | TOL |
| PSMB9 | Proteasome subunit | NM_002800 | Blood | TOL |
| N33 | Putative prostate cancer tumor suppressor | NM_006765 | Blood | TOL |
| DP1 | Polyposis locus protein 1 (DP1) | NM_005669 | Blood | TOL |
| TFDP1 | Transcription factor Dp-1 | NM_007111 | Blood | TOL |
| OSF-2 | OSF-2 osteoblast specific factor 2 | NM_000358 | Blood | TOL |
| COL3A1 | Collagen, type III, alpha 1 | NM_000090 | Blood | TOL |
| TIMP3 | TIMP3 tissue inhibitor of metalloproteinase 3 | NM_000362 | Blood | TOL |
| SPP1 | Osteopontin, early T-lymphocyte activation 1 | NM_000582 | Blood | TOL |
| NQO1 | NQO1 NAD(P)H dehydrogenase | NM_000903 | Blood | TOL |
| TOP2A | Topoisomerase (DNA) II alpha 170 kDa | NM_001067 | Blood | TOL |
| CCND2 | Cyclin D2 | NM_001759 | Blood | TOL |
| CNN3 | CNN3 calponin 3, acidic AI969128 | NM_001839 | Blood | TOL |
| COL6A1 | Collagen, type VI, alpha 1 | NM_001848 | Blood | TOL |
| CTGF | Connective tissue growth factor | NM_001901 | Blood | TOL |
| EGR1 | Early growth response 1 (EGR1) | NM_001964 | Blood | TOL |
| SDC2 | Syndecan 2 | NM_002998 | Blood | TOL |
| TCF3 | Transcription factor 3 | NM_003200 | Blood | TOL |
| TFAP2C | Transcription factor AP-2 gamma | NM_003222 | Blood | TOL |
| NRP1 | Neuropilin 1 | NM_003873 | Blood | TOL |
| GITR | TNF receptor superfamily18 (TNFRSF18) | NM_004195 | Blood | TOL |
| COL6A3 | Collagen, type VI, alpha 3 | NM_004369 | Blood | TOL |
| EPHA2 | EPHA2 EphA2 | NM_004431 | Blood | TOL |
| PDE1A | ARHE ras homolog gene family | NM_005168 | Blood | TOL |
| FAT | Tumor suppressor homolog 1 | NM_005245 | Blood | TOL |
| KIFC3 | Kinesin family member C3 | NM_005550 | Blood | TOL |
| NR2F1 | Nuclear receptor subfamily 2F1 | NM_005654 | Blood | TOL |
| CAP2 | CAP, adenylate cyclase-associated 2 | NM_006366 | Blood | TOL |
| BACE2 | Beta-site APP-cleaving enzyme 2 | NM_012105 | Blood | TOL |
| FADS1 | Fatty acid desaturase 1 | NM_013402 | Blood | TOL |
| MELK | Maternal embryonic leucine zipper kinase | NM_014791 | Blood | TOL |
| DKK3 | Dickkopf homolog 3 (Xenopus laevis) | NM_015881 | Blood | TOL |
| CCNB1 | Cyclin B1 | NM_031966 | Blood | TOL |
| CALD1 | Caldesmon 1 | NM_033138 | Blood | TOL |
| CASP1 | Caspase 1, (interleukin 1b convertase) | NM_033292 | Blood | TOL |
| KNSL5 | Kinesin-like 5 (mitotic kinesin-like protein 1) | NM_138555 | Blood | TOL |
| STK6 | Serine/threonine kinase 6 | NM_198433 | Blood | TOL |
| CD59 | CD59 antigen p18-20 | NM_203330 | Blood | TOL |
| FN1 | Fibronectin 1 | NM_212482 | Blood | TOL |
| SERPINE2 | Serine proteinase inhibitor | NM_006216 | Blood | TOL |
| CDH2 | Cadherin 2, type 1, N-cadherin | NM_001792 | Blood | TOL |
| CCNE1 | Cyclin E1 | NM_001238 | Blood | TOL |
| SEMA3F | Ig short basic domain, secreted | NM_004186 | Blood | TOL |
| MAD2L1 | MAD2 mitotic arrest deficient-like 1 | NM_002358 | Blood | TOL |
| CYR61 | Cysteine-rich, angiogenic inducer, 61 | NM_001554 | Blood | TOL |

TABLE 3-continued

Genes of known function of prognostic value compiled for a custom transplantation chip (TxChip VI).

| Symbol | Name | mRNA | Tissue | Study |
|---|---|---|---|---|
| TNFRSF7 | CD27 TNF receptor superfamily 7 | NM_001242 | Blood | TOL |
| FOXP3 | Forkhead box P3 (FOXP3), mRNA | NM_014009 | Blood | TOL |
| ABCA4 | ATP-binding cassette, sub-family A (ABC1) | NM_000350 | Biopsy | Control |
| HNK-1 | HNK-1 sulfotransferase | AF033827 | Biopsy | Control |
| UCP2 | Uncoupling protein 2 | NM_003355 | Biopsy | Control |
| DAB2 | Mitogen-responsive phosphoprotein | NM_001343 | Biopsy | Control |
| AQP3 | Aquaporin 3 | NM_004925 | Biopsy | Control |
| CRABP1 | Cellular retinoic acid binding protein 1 | NM_004378 | Biopsy | Control |
| KCNAB2 | Potassium voltage-gated channel | NM_003636 | Biopsy | Control |
| TNNT2 | Troponin T2, cardiac | NM_000364 | Biopsy | Control |
| APP | Amyloid beta (A4) precursor protein | NM_000484 | Biopsy | Control |
| FABP3 | Fatty acid binding protein 3 | NM_004102 | Biopsy | Control |
| PODXL | Podocalyxin-like | NM_005397 | Biopsy | Control |
| ALPI | Alkaline phosphatase, intestinal | NM_001631 | Biopsy | Control |
| MAPT | Microtubule-associated protein tau | NM_005910 | Biopsy | Control |
| KHK | Ketohexokinase (fructokinase) | NM_000221 | Biopsy | Control |
| 18S | 18s ribosomal RNA | M10098 | All | Control |
| ACTB | Actin, beta | NM_001101 | All | Control |
| GAPD | Glyceraldehyde-3-phosphate dehydrogenase | NM_002046 | All | Control |
| GSUSB | Glucuronidase, beta | NM_000181 | All | Control |
| HPRT1 | Hypoxanthine phosphoribosyltransferase 1 | NM_000194 | All | Control |
| SCYA3 | Chemokine (C—C motif) ligand 3 | NM_002983 | All | Control |
| LMO2 | LIM domain only 2 (LMO2) | NM_005574 | All | Control |
| BCL6 | B-cell CLL/lymphoma 6 | NM_001706 | All | Control |
| IkB2 | NFkB enhancer in B-cells inhibitor | NM_020529 | All | Control |
| APC | Adenomatosis polyposis coli | NM_000038 | All | Control |
| BAG2 | BCL2-associated athanogene 2 (BAG2) | NM_004282 | All | Control |
| CREBBP | CREB binding protein | NM_004380 | All | Control |
| KLRB1 | Killer cell lectin-like receptor B1 | NM_002258 | All | Control |
| TRADD | TNFRSF1A-associated via death domain | NM_003789 | All | Control |
| CXCL14 | Chemokine (C—X—C motif) ligand 14 | NM_004887 | All | Control |
| IL1A | Interleukin 1, alpha | NM_000575 | All | Control |
| MMP1 | Matrix metalloproteinase 1 | NM_002421 | All | Control |
| MMP9 | Matrix metalloproteinase 9 | NM_004994 | All | Control |
| VEGFC | Vascular endothelial growth factor C | NM_005429 | All | Control |
| CD8A | CD8 antigen, alpha polypeptide (p32) | NM_171827 | Blood | Control |
| CD3G | CD3G antigen, gamma (TiT3 complex) | NM_000073 | Blood | Control |
| CD44 | CD44 antigen | NM_000610 | Blood | Control |
| CD4 | CD4 antigen (p55) | NM_000616 | Blood | Control |
| CD3D | CD3D antigen, delta (TiT3 complex) | NM_000732 | Blood | Control |
| CD3E | CD3E antigen, epsilon (TiT3 complex) | NM_000733 | Blood | Control |
| CD3Z | CD3Z antigen, zeta (TiT3 complex) | NM_000734 | Blood | Control |
| CD19 | CD19 antigen | NM_001770 | Blood | Control |
| B220 | Protein tyrosine phosphatase receptor | NM_002838 | Blood | Control |
| CD138 | CD138 syndecan 1 (SDC1) | NM_002997 | Blood | Control |
| CD43 | Sialophorin (CD43) | NM_003123 | Blood | Control |
| CD8B1 | CD8 antigen, beta polypeptide 1 (p37) | NM_004931 | Blood | Control |
| API5 | Apoptosis inhibitor 5 | NM_006595 | All | Lit. |
| Axin1 | Axin 1 | NM_003502 | All | Lit. |
| Axin2 | Axin 2 (conductin, axil) | NM_004655 | All | Lit. |
| BAD | BCL2-antagonist of cell death | NM_032989 | All | Lit. |
| BIK | BCL2-interacting killer (apoptosis-inducing) | NM_001197 | All | Lit. |
| BMP4 | Bone morphogenetic protein 4 | NM_001202 | All | Lit. |
| BTG1 | B-cell translocation gene 1 | NM_001731 | All | Lit. |
| CASP10 | Caspase 10, apoptosis-related cysteine protease | NM_001230 | All | Lit. |
| CASP3 | Caspase 3, apoptosis-related cysteine protease | NM_004346 | All | Lit. |
| CASP4 | Caspase 4, apoptosis-related cysteine protease | NM_001225 | All | Lit. |
| CASP7 | Caspase 7, apoptosis-related cysteine protease | NM_001227 | All | Lit. |
| CASP9 | Caspase 9, apoptosis-related cysteine protease | NM_001229 | All | Lit. |
| CCL18 | Chemokine (C—C motif) ligand 18 | NM_002988 | All | Lit. |
| CD161 | Killer cell lectin-like receptor B1 | BC027885 | All | Lit. |
| CD20 | Membrane-spanning 4A1 | NM_152866 | All | Lit. |
| CD22 | CD22 antigen | NM_001771 | All | Lit. |
| CD48 | CD48 antigen (B-cell membrane protein) | NM_001778 | All | Lit. |
| CD80 | CD80 antigen (B7-1 antigen) | NM_005191 | All | Lit. |
| CDA08 | T-cell immunomodulatory protein | NM_030790 | All | Lit. |
| CDC2 | Cell division cycle 2, G1 to S and G2 to M | NM_001786 | All | Lit. |
| CDw108 | Semaphorin Ig and GPI membrane anchor 7A, | NM_003612 | All | Lit. |
| CDW52 | CDW52 antigen (CAMPATH-1 antigen) | NM_001803 | All | Lit. |
| CIS4 | STAT induced STAT inhibitor-4 | NM_004232 | All | Lit. |
| CTLA4 | Cytotoxic T-lymphocyte-associated protein 4 | NM_005214 | All | Lit. |
| DAD1 | Defender against cell death 1 | NM_001344 | All | Lit. |
| DAP3 | Death associated protein 3 | NM_033657 | All | Lit. |
| DAPK2 | Death-associated protein kinase 2 | NM_014326 | All | Lit. |
| DAPK3 | Death-associated protein kinase 3 | NM_001348 | All | Lit. |

TABLE 3-continued

Genes of known function of prognostic value compiled for a custom transplantation chip (TxChip VI).

| Symbol | Name | mRNA | Tissue | Study |
|---|---|---|---|---|
| DAXX | Death-associated protein 6 | NM_001350 | All | Lit. |
| EBF | Early B-cell factor | NM_024007 | All | Lit. |
| FCGR1A | Fc fragment of IgG (receptor for CD64) | NM_000566 | All | Lit. |
| GADD45B | Growth arrest and DNA-damage-inducible | NM_015675 | All | Lit. |
| GSR | Glutathione reductase | NM_000637 | All | Lit. |
| GZMA | Granzyme A | NM_006144 | All | Lit. |
| GZMB | Granzyme B | NM_004131 | All | Lit. |
| Gzmc | Granzyme C | M18459 | All | Lit. |
| GZMK | Granzyme K | NM_002104 | All | Lit. |
| HLA-E | MHC class I, E | NM_005516 | All | Lit. |
| ICAM1 | Intercellular adhesion molecule 1 (CD54) | NM_000201 | All | Lit. |
| ICAM3 | Intercellular adhesion molecule 3 | NM_002162 | All | Lit. |
| IFI16 | Interferon, gamma-inducible protein 16 | NM_005531 | All | Lit. |
| IFI35 | Interferon-induced protein 35 | NM_005533 | All | Lit. |
| IFNG | Interferon, gamma | NM_000619 | All | Lit. |
| IGBP1 | Ig (CD79A) binding protein 1 | NM_001551 | All | Lit. |
| IGJ | Ig J polypeptide, linker protein | NM_144646 | All | Lit. |
| IK | IK cytokine, down-regulator of HLA II | NM_006083 | All | Lit. |
| IL2RA | Interleukin 2 receptor, alpha | NM_000417 | All | Lit. |
| IL4R | Interleukin 4 receptor | NM_000418 | All | Lit. |
| IL6 | Interleukin 6 (interferon, beta 2) | NM_000600 | All | Lit. |
| IL7R | Interleukin 7 receptor | NM_002185 | All | Lit. |
| IL8RB | Interleukin 8 receptor, beta | NM_001557 | All | Lit. |
| IRF1 | Interferon regulatory factor 1 | NM_002198 | All | Lit. |
| ITGAE | Integrin, alpha E (CD103) | NM_002208 | All | Lit. |
| JAK1 | Janus kinase 1 | NM_002227 | All | Lit. |
| JAK2 | Janus kinase 2 | NM_004972 | All | Lit. |
| MADH2 | SMAD, mothers against DPP | NM_005901 | All | Lit. |
| MAPK3 | Mitogen-activated protein kinase 3 | NM_002746 | All | Lit. |
| MDM2 | p53 binding protein | NM_002392 | All | Lit. |
| MHC2TA | MHC class II transactivator | NM_000246 | All | Lit. |
| NK4 | Natural killer cell transcript 4 | NM_004221 | All | Lit. |
| NMI | N-myc (and STAT) interactor | NM_004688 | All | Lit. |
| PCNA | Proliferating cell nuclear antigen | NM_002592 | All | Lit. |
| PDCD2 | Programmed cell death 2 | NM_002598 | All | Lit. |
| PDCD7 | Programmed cell death 7 | NM_005707 | All | Lit. |
| PDCD8 | Programmed cell death 8 | NM_004208 | All | Lit. |
| PDGFRB | Platelet-derived growth factor receptor | NM_002609 | All | Lit. |
| RhoA | Ras homolog gene family, member A | NM_001664 | All | Lit. |
| SIMRP7 | Multidrug resistance-associated protein 7 | NM_033450 | All | Lit. |
| SOD2 | Superoxide dismutase 2, mitochondrial | NM_000636 | All | Lit. |
| SSI-1 | suppressor of cytokine signaling 1 | NM_003745 | All | Lit. |
| STAT2 | Signal transducer2, 113 kDa | NM_005419 | All | Lit. |
| STAT3 | Signal transducer 3 (acute-phase response factor) | NM_139276 | All | Lit. |
| STAT4 | Signal transducer 4 | NM_003151 | All | Lit. |
| STAT5A | Signal transducer 5A | NM_003152 | All | Lit. |
| STAT5B | Signal transducer a5B | NM_012448 | All | Lit. |
| STK21 | Rho-interacting | NM_007174 | All | Lit. |
| TA-LRRP | TNF receptor-associated factor 6 | NM_145803 | All | Lit. |
| TCRA | T-cell receptor active alpha-chain | M12423 | All | Lit. |
| TCRB | T cell receptor beta locus | X60096 | All | Lit. |
| TCRD | T-cell receptor delta chain (VJC-region) | M21624 | All | Lit. |
| TCRG | T cell receptor gamma locus | X06774 | All | Lit. |
| TFRC | Transferrin receptor (p90, CD71) | NM_003234 | All | Lit. |
| TGFA | Transforming growth factor, alpha | NM_003236 | All | Lit. |
| TGFB2 | Transforming growth factor, beta 2 | NM_003238 | All | Lit. |
| THBS2 | Thrombospondin 2 | NM_003247 | All | Lit. |
| TIA1 | Cytotoxic granule-associated RNA binding | NM_022173 | All | Lit. |
| TIEG2 | TGFB inducible early growth response 2 | NM_003597 | All | Lit. |
| TLR5 | Toll-like receptor 5 | NM_003268 | All | Lit. |
| TNFRSF1A | TNF receptor superfamily, member 1A | NM_001065 | All | Lit. |
| TNFRSF1B | TNF receptor superfamily, member 1B | NM_001066 | All | Lit. |
| TNFSF7 | TNF (ligand) superfamily, member 7 | NM_001252 | All | Lit. |
| TP53BP1 | Tumor protein p53 binding protein, 1 | NM_005657 | All | Lit. |
| TP53BP2 | Tumor protein p53 binding protein, 2 | NM_005426 | All | Lit. |
| TRAF1 | TNF receptor-associated factor 1 | NM_005658 | All | Lit. |
| TRAF2 | TNF receptor-associated factor 2 | NM_021138 | All | Lit. |
| TRAF3 | TNF receptor-associated factor 3 | NM_003300 | All | Lit. |
| TRAF4 | TNF receptor-associated factor 4 | NM_004295 | All | Lit. |
| TRAP1 | TNF receptor-associated protein 1 | NM_004257 | All | Lit. |
| TTK | TTK protein kinase | NM_003318 | All | Lit. |
| UBE1L | Ubiquitin-activating enzyme E1-like | NM_003335 | All | Lit. |
| VPREB3 | Pre-B lymphocyte gene 3 | NM_013378 | All | Lit. |
| WNT1 | MMTV integration site (WNT1) | NM_005430 | All | Lit. |
| ACE1 | Ig receptor (PIGR) IgA nephritis | NM_002644 | All | Lit. |

TABLE 3-continued

Genes of known function of prognostic value compiled for a custom transplantation chip (TxChip VI).

| Symbol | Name | mRNA | Tissue | Study |
|---|---|---|---|---|
| BAX | BCL2-associated X protein | NM_138763 | All | Lit. |
| BCL2 | B-cell CLL/lymphoma 2 | NM_000633 | All | Lit. |
| C3 | Complement component 3 | NM_000064 | All | Lit. |
| CD28 | CD28 antigen (Tp44) | NM_006139 | All | Lit. |
| CD86 | CD86 antigen (B7-2 antigen) | NM_006889 | All | Lit. |
| ICOS | Inducible T-cell co-stimulator | NM_012092 | All | Lit. |
| IL10 | Interleukin 10 | NM_000572 | All | Lit. |
| IL15 | Interleukin 15 | NM_000585 | All | Lit. |
| IL2 | Interleukin 2 | NM_000586 | All | Lit. |
| IL4 | Interleukin 4 | NM_000589 | All | Lit. |
| IL7 | Interleukin 7 | NM_000880 | All | Lit. |
| IL8 | Interleukin 8 | NM_000584 | All | Lit. |
| PRF1 | Perforin 1 (pore forming protein) | NM_005041 | All | Lit. |
| RANTES | Chemokine (C—C motif) ligand 5 (CCL5) | NM_002985 | All | Lit. |
| TBET | Th1-specific T-box transcription factor | NM_013351 | All | Lit. |
| TGFB1 | TGF beta 1 | NM_000660 | All | Lit. |
| TNF | TNF superfamily, member 2 | NM_000594 | All | Lit. |
| TNFB | Lymphotoxin alpha (TNF1 or LTA) | NM_000595 | All | Lit. |
| TNFRSF5 | CD40 TNF receptor superfamily 5 | NM_001250 | All | Lit. |
| TNFRSF6 | CD95 = Fas TNF receptor superfamily 6 | NM_000043 | All | Lit. |
| VEGF | Vascular endothelial growth factor | NM_003376 | All | Lit. |

In certain embodiments, a collection of genes from Table 3 is assayed, where in these embodiments the number of genes from Table 3 may be at least about 5%, at least about 10%, at least about 25%, at least about 50%, at least about 75%, at least about 90% or more, including all of the genes from Table 3.

In certain embodiments, the expression profile obtained is a genomic or nucleic acid expression profile, where the amount or level of one or more nucleic acids in the sample is determined, e.g., the nucleic acid transcript of the gene of interest. In these embodiments, the sample that is assayed to generate the expression profile employed in the diagnostic methods is one that is a nucleic acid sample. The nucleic acid sample includes a plurality or population of distinct nucleic acids that includes the expression information of the phenotype determinative genes of interest of the cell or tissue being diagnosed. The nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as is, amplified, employed to prepare cDNA, cRNA, etc., as is known in the differential expression art. In certain embodiments, the sample is prepared from a cell or tissue harvested from a subject to be diagnosed, e.g., via biopsy of tissue, using standard protocols, where cell types or tissues from which such nucleic acids may be generated include any tissue in which the expression pattern of the to be determined phenotype exists, including, but not limited to, peripheral blood lymphocyte cells, etc, as reviewed above.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array-based gene expression profile generation protocols. In certain embodiments, such applications are hybridization assays in which a nucleic acid array that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative.

Alternatively, non-array based methods for quantitating the levels of one or more nucleic acids in a sample may be employed, including quantitative PCR, and the like.

Where the expression profile is a protein expression profile, any convenient protein quantitation protocol may be employed, where the levels of one or more proteins in the assayed sample are determined. Representative methods include, but are not limited to: proteomic arrays, flow cytometry, standard immunoassays (e.g., ELISA assays), protein activity assays, including multiplex protein activity assays, etc.

Following obtainment of the expression profile from the sample being assayed, the expression profile is compared with a reference or control profile to determine the particular graft tolerant/intolerant phenotype of the cell or tissue, and therefore host, from which the sample was obtained/derived. The terms "reference" and "control" as used herein mean a standardized pattern of gene expression or levels of expression of certain genes to be used to interpret the expression signature of a given patient and assign a graft tolerant/intolerant phenotype thereto. The reference or control profile may be a profile that is obtained from a cell/tissue known to have the desired phenotype, e.g., tolerant phenotype, and therefore may be a positive reference or control profile. In addition, the reference/control profile may be from a cell/tissue known to not have the desired phenotype, e.g., an intolerant phenotype, and therefore be a negative reference/control profile.

In certain embodiments, the obtained expression profile is compared to a single reference/control profile to obtain information regarding the phenotype of the cell/tissue being assayed. In yet other embodiments, the obtained expression profile is compared to two or more different reference/control profiles to obtain more in depth information regarding the phenotype of the assayed cell/tissue. For example, the obtained expression profile may be compared to a positive and negative reference profile to obtain confirmed information regarding whether the cell/tissue has the phenotype of interest.

The comparison of the obtained expression profile and the one or more reference/control profiles may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above.

The comparison step results in information regarding how similar or dissimilar the obtained expression profile is to the control/reference profile(s), which similarity/dissimilarity information is employed to determine the phenotype of the cell/tissue being assayed and thereby evaluate graft survival in the subject. For example, similarity with a positive control indicates that the assayed cell/tissue has a graft survival phenotype. Likewise, similarity with a negative control indicates that the assayed cell/tissue has a graft loss phenotype.

Figure 4:
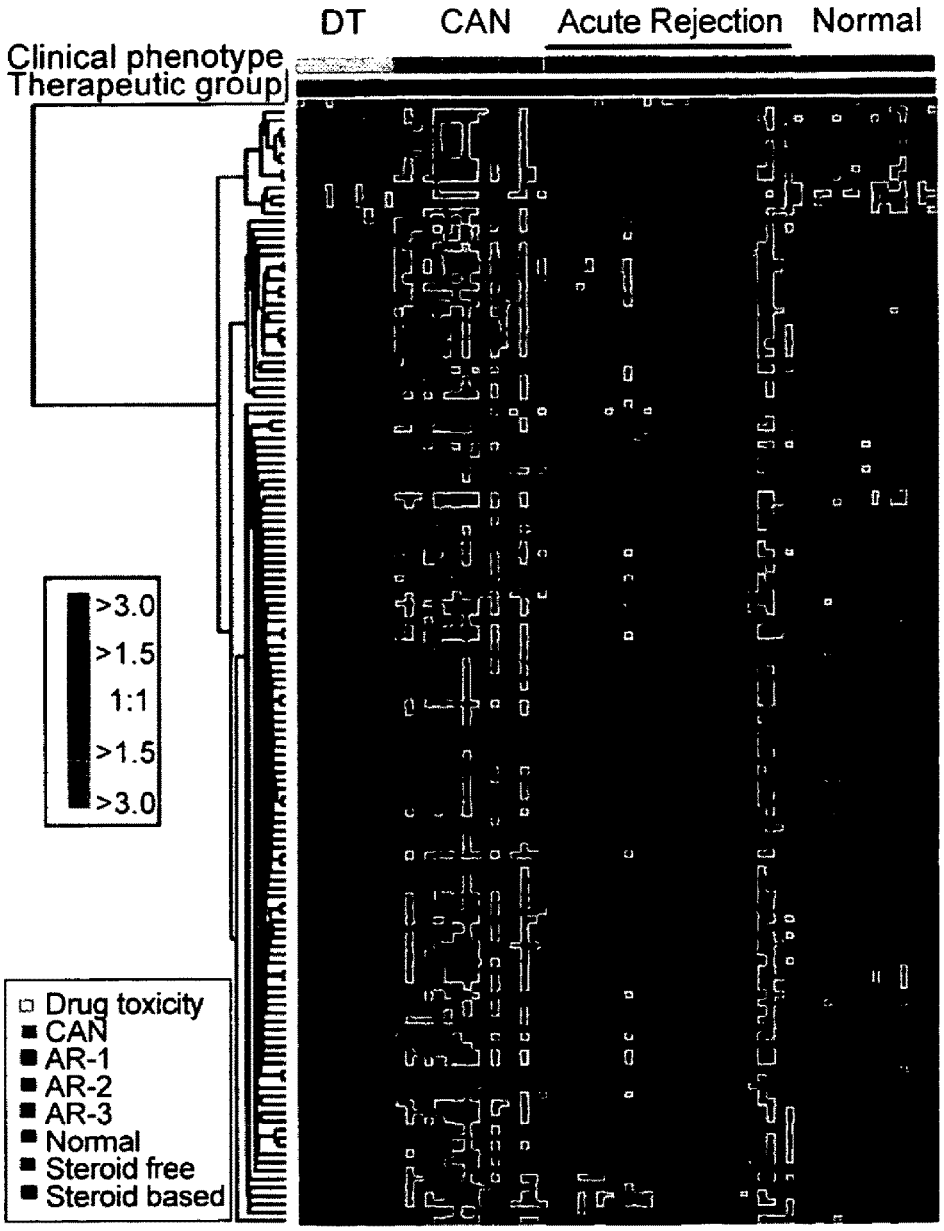
FIG. 4. Demonstrates that gene expression is generally uniform/consistent across the full clinical groups analyzed as the gene expression levels segregate well within patient groups.

Depending on the type and nature of the reference/control profile(s) to which the obtained expression profile is compared, the above comparison step yields a variety of different types of information regarding the cell/tissue that is assayed. As such, the above comparison step can yield a positive/negative determination of a graft survival phenotype of an assayed cell/tissue. In many embodiments, the above-obtained information about the cell/tissue being assayed is employed to diagnose a host, subject or patient with respect to graft survival, as described above. In certain embodiments, the determination/prediction of graft survival and loss can be coupled with a determination of additional characteristics of the graft and function thereof. For example, in certain embodiments one can predict not only whether graft loss will occur, but the mechanism of graft loss, e.g., via CAN or DT. The first 9 genes in the cluster illustrated in FIG. 4 are highly-differentially expressed between CAN and DT. As such, evaluating one or more of these genes permits these two overlapping conditions to be readily distinguished, such that one can readily determine the presence of CAN or DT.

The subject methods further find use in pharmacogenomic applications. In these applications, a subject/host/patient is first diagnosed for graft function according to the subject invention, and then treated using a protocol determined, at least in part, on the results of the diagnosis. For example, a host may be evaluated for the presence of absence of the graft survival phenotype using a protocol such as the diagnostic protocol described in the preceding section. The subject may then be treated using a protocol whose suitability is determined using the results of the diagnosis step. In embodiments, where the host is evaluated for the presence or absence of CAN or DT, treatment protocols may correspondingly be adjusted based on the obtained results. For example, where the subject methods are employed to determine the presence of CAN, immunosuppressive therapy can be modulated, e.g., increased or drugs changed, as is known in the art for the treatment of CAN. Likewise, where the subject methods are employed and detect the presence of DT, the immunosuppressive therapy can be reduced in order to treat the DT. In practicing the subject methods, a subject is typically screened for the presence of a graft survival or loss phenotype following receipt of a graft or transplant. The subject may be screened once or serially following transplant receipt, e.g., weekly, monthly, bimonthly, half-yearly, yearly, etc. In certain embodiments, the subject is screened following occurrence of acute rejection (AR). In such embodiments, the methods are employed to evaluate, e.g., predict, ultimate graft loss or survival in the subject following AR.

The subject methods may be employed with a variety of different types of transplant subjects. In many embodiments, the subjects are within the class mammalian, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the animals or hosts, i.e., subjects (also referred to herein as patients) will be humans.

The methods may be used to evaluate survival of a variety of different types of grafts. Grafts of interest include, but are not limited to: transplanted heart, kidney, lung, liver, pancreas, pancreatic islets, brain tissue, stomach, large intestine, small intestine, cornea, skin, trachea, bone, bone marrow, muscle, bladder or parts thereof.

Databases of Expression Profiles of Phenotype Determinative Genes

Also provided are databases of expression profiles of graft survival and/or graft loss phenotype determinative genes. Such databases will typically comprise expression profiles of various cells/tissues having graft tolerant phenotypes, negative expression profiles, etc., where such profiles are further described below.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. One format for an output means ranks expression profiles possessing varying degrees of similarity to a reference expression profile. Such presentation provides a skilled artisan with a ranking of similarities and identifies the degree of similarity contained in the test expression profile.

Reagents, Systems and Kits

Also provided are reagents, systems and kits thereof for practicing one or more of the above-described methods. The subject reagents, systems and kits thereof may vary greatly. Reagents of interest include reagents specifically designed for use in production of the above-described expression profiles of phenotype determinative genes, i.e., a gene expression evaluation element made up of one or more reagents. The term system refers to a collection of reagents, however compiled, e.g., by purchasing the collection of reagents from the same or different sources. The term kit refers to a collection of reagents provided, e.g., sold, together.

One type of such reagent is an array of probe nucleic acids in which the phenotype determinative genes of interest are represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

In certain embodiments, the arrays include probes for at least 1 of the genes listed in Tables 1 and/or 2. In certain embodiments, the number of genes that are from Tables 1 and/or 2 that is represented on the array is at least 5, at least 10, at least 25, at least 50, at least 75 or more, including all of the genes listed in Tables 1 and/or 2. The subject arrays may include only those genes that are listed in Tables 1 and/or 2, or they may include additional genes that are not listed in Tables 1 and/or 2, such as probes for genes whose expression pattern can be used to evaluate additional transplant characteristics, including but not limited to: acute rejection; chronic allograft injury (chronic rejection) in blood; immunosuppressive drug toxicity or adverse side effects including drug-induced hypertension; age or body mass index associated genes that correlate with renal pathology or account for differences in recipient age-related graft acceptance; immune tolerance markers in whole blood; genes found in literature surveys with immune modulatory roles that may play a role in transplant outcomes (see e.g., Table 3 for a list of representative additional genes); as well as other array assay function related genes, e.g., for assessing sample quality (3'- to 5'-bias in probe location), sampling error in biopsy-based studies, cell surface markers, and normalizing genes for calibrating hybridization results; and the like. Where the subject arrays include probes for such additional genes, in certain embodiments the number % of additional genes that are represented and are not directly or indirectly related to transplantation does not exceed about 50%, usually does not exceed about 25%. In certain embodiments where additional genes are included, a great majority of genes in the collection are transplant characterization genes, where by great majority is meant at least about 75%, usually at least about 80% and sometimes at least about 85, 90, 95% or higher, including embodiments where 100% of the genes in the collection are phenotype determinative genes. Transplant characterization genes are genes whose expression can be employed to characterize transplant function in some manner, e.g., presence of rejection, etc.

Another type of reagent that is specifically tailored for generating expression profiles of phenotype determinative genes is a collection of gene specific primers that is designed to selectively amplify such genes. Gene specific primers and methods for using the same are described in U.S. Pat. No. 5,994,076, the disclosure of which is herein incorporated by reference. Of particular interest are collections of gene specific primers that have primers for at least 1 of the genes listed in one Tables 1 and/or 2, often a plurality of these genes, e.g., at least 2, 5, 10, 15 or more. In certain embodiments, the number of genes that are from Tables 1 and/or 2 that have primers in the collection is at least 5, at least 10, at least 25, at least 50, at least 75 or more, including all of the genes listed in Tables 1 and/or 2. The subject gene specific primer collections may include only those genes that are listed in Tables 1 and/or 2, or they may include primers for additional genes that are not listed in Tables 1 and/or 2, such as probes for genes whose expression pattern can be used to evaluate additional transplant characteristics, including but not limited to: acute rejection; chronic allograft injury (chronic rejection) in blood; immunosuppressive drug toxicity or adverse side effects including drug-induced hypertension; age or body mass index associated genes that correlate with renal pathology or account for differences in recipient age-related graft acceptance; immune tolerance markers in whole blood; genes found in literature surveys with immune modulatory roles that may play a role in transplant outcomes (see e.g., Table 3 for a list of representative additional genes); as well as other array assay function related genes, e.g., for assessing sample quality (3'- to 5'-bias in probe location), sampling error in biopsy-based studies, cell surface markers, and normalizing genes for calibrating hybridization results; and the like. Where the subject arrays include probes for such additional genes, in certain embodiments the number % of additional genes that are represented and are not directly or indirectly related to transplantation does not exceed about 50%, usually does not exceed about 25%. In certain embodiments where additional genes are included, a great majority of genes in the collection are transplant characterization genes, where by great majority is meant at least about 75%, usually at least about 80% and sometimes at least about 85, 90, 95% or higher, including embodiments where 100% of the genes in the collection are phenotype determinative genes.

The systems and kits of the subject invention may include the above-described arrays and/or gene specific primer collections. The systems and kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The subject systems and kits may also include a phenotype determination element, which element is, in many embodiments, a reference or control expression profile that can be employed, e.g., by a suitable computing means, to make a phenotype determination based on an "input" expression profile, e.g., that has been determined with the above described gene expression evaluation element. Representative phenotype determination elements include databases of expression profiles, e.g., reference or control profiles, as described above.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Introduction

The objective of this study was to determine whether gene expression markers could be identified in RNA extracted from peripheral blood leukocytes (PBL) or renal biopsies predictive of future graft loss following AR.

II. Array Experiments

Each microarray contained approximately 32,000 DNA spots representing approximately 12,440 human genes. Total RNA was isolated (Tri Reagent; MRC Inc., Cincinnati, Ohio) from buffy coats isolated from whole blood samples. A common reference RNA pool (Perou et al., Nature (2000) 406:747-52) was used as an internal standard. Sample or reference RNA were subjected to two successive rounds of amplification before hybridization to microarrays using an improved protocol based on the method described by Wang et al (please provide entire cite). Array data for 62 renal biopsy samples and 56 whole blood samples were stored in the Stanford Microarray database (Sherlock et al., Nuc. Acids Res. (2001) 29:152-55) and gene lists filtered at retrieval to provide expression markers with high fidelity. The two groups of samples were analyzed in two separate studies. All PBL were used for initial unsupervised hierarchical clustering (Eisen et al., Proc. Nat'l Acad. Sci. USA (1998) 95:14863-8), for subsequent supervised analyses between groups (Significance Analysis of Microarrays; SAM (Tusher et al., Proc. Nat'l Acad. Sci. USA (2001) 98:5116-21).

III. Customizing a Minimal Gene-Set for AR Class Prediction and Risk Assessment We used Predictive Analysis of Microarrays (PAM) (Tusher et al., supra) to identify only 97 genes within the renal biopsy dataset, all having >5-fold difference in expression level, which classify our learning set of 26 AR samples with 100% concordance to assigned phenotype. Another analysis using a larger set of 3,170 differentially expressed genes identifies the 33 classifiers with similar power (FIGS. 1A and 1B). Reproducibility of the diagnostic signature, in particular within the majority of the AR-1 samples, is evident by the short branches in the cluster dendogram. AR expression overlaps with the innate immune response to infection, as evidenced by cluster analysis and by differential expression of several TGF-β-modulated genes including RANTES, MIC-1, several cytokines, chemokines, and cell-adhesion molecules. AR-1 is the most severe class with the highest rate of graft loss and highest expression of B-cell specific genes. AR-2 resembles a drug-toxicity signature and also co-clusters with patients with active viral infections. The most striking feature of AR-3 is the expression of genes involved in cellular proliferation and cell cycling suggesting active tissue repair and regeneration. The presence of proliferating-cell nuclear antigen (PCNA), a marker of cell proliferation, was confirmed in all AR-3 samples tested (Sarwal et al. New Engl. J. Med. 2003 349(2):125-38).

The PAM classification scores grouped the samples with 100% concordance to assigned classes and reported scores are aligned with the clustered samples (FIG. 1B). In addition, all 33 genes selected by PAM have Significance Analysis of Microarrays significance scores of 0.09% or lower suggesting that they would be highly significant biomarkers for a customized array list.

A. PAM Class Prediction—

Figure 2:
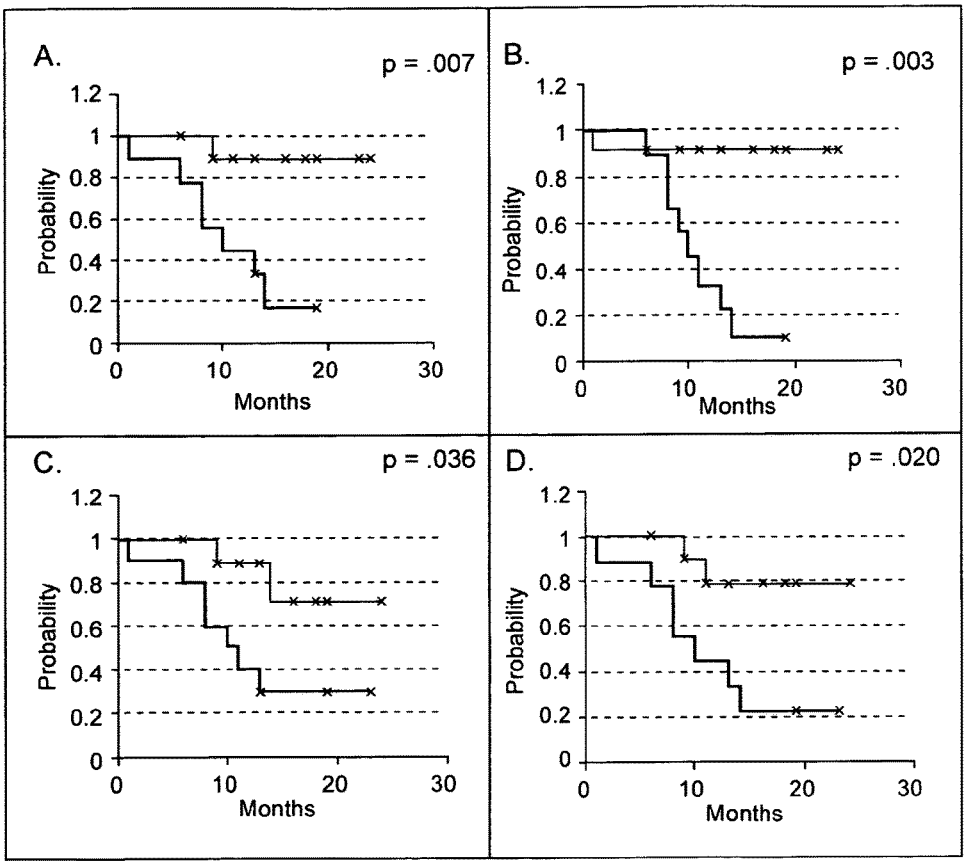
FIG. 2. Kaplan-Meier survival analysis for graft loss (red) and no-loss (blue). The genes include ICAM5 (FIG. 2A; p=0.007), IL6R (FIG. 2B; p=0.003), STAT1 (FIG. 2C; p=0.036), and STAT6 (FIG. 2D (p=0.020).

PAM class prediction has also proven to be a powerful approach to identify putative biomarkers for graft recovery and graft loss. We have used both Cox-regression and PAM to correlate expression differences with graft outcome with good success. Both methods yield significant results in Kaplan-Meier survival analysis although at the initial 2-year follow-up genes identified by PAM also yield greater significance. (FIG. 2—Kaplan-Meier survival analysis for graft loss (red) and no-loss (blue. The genes include ICAM5-FIG. 2A; (p=0.007), IL6R; FIG. 2B; (p=0.003), STAT1; FIG. 2C; (p=0.036), and STAT6; FIG. 2D; (p=0.020)).

The gene signature is dominated by increased expression of cell adhesion genes, selected cytokines, B-cell genes, representatives in the STAT signaling pathway and several immune response genes including multiple representatives of both class I and class II HLA genes.

Representative genes include those from HLA class I (HLA-F, HLA-G), HLA class II (HLA-DRB1, HLA-DRB5, HLA-DRB4), signal transducers (STAT1, STAT6), immunoglobulin genes (IGKC, IGHG3), and 2 interferon gamma induced genes (ICAM5, IL6R).

A similar approach was used to identify graft-loss markers in whole blood samples. The list of the most highly-predictive significant genes in blood is summarized in Table 4, including the Kaplan-Meier survival significance score.

TABLE 4

| Symbol | Gene | Unigene ID | Fold Loss/ No-loss | p-value |
|---|---|---|---|---|
| HIST1H2BC | Histone 1, H2bc | Hs.356901 | −3.46 | 0.00018 |
| IGHG3 | Ig heavy constant gamma 3 (G3m marker) | Hs.413826 | 4.14 | 0.00134 |
| AHSA2 | Activator of heat shock ATPase | Hs.122440 | 2.91 | 0.00041 |
| TNFRSF10D | TNF receptor superfamily 10b | Hs.129844 | −2.55 | 0.00010 |
| MAPK9 | Mitogen-activated protein kinase 9 | Hs.348446 | 8.14 | 0.00444 |
| IFNAR2 | Interferon (alpha, beta and omega) receptor 2 | Hs.86958 | −2.37 | 0.01760 |
| TM4SF9 | Transmembrane 4 superfamily member 9 | Hs.8037 | −15.29 | 0.00580 |
| MIF | Macrophage migration inhibitory factor | Hs.407995 | −2.31 | 0.00674 |
| SCYE1 | Small inducible cytokine (Monocyte-activating) | Hs.105656 | 2.51 | 0.00154 |
| MAPK1 | Mitogen-activated protein kinase 1 | Hs.324473 | −2.32 | 0.00019 |
| TGFBR3 | TGFb receptor III (betaglycan) | Hs.342874 | −2.94 | 0.00318 |
| IGKC | Immunoglobulin kappa constant | Hs.377975 | 2.35 | 0.00290 |
| IL1R2 | Interleukin 1 receptor, type II | Hs.25333 | −4.06 | 0.01762 |
| IGL | Immunoglobulin lambda light chain | | 3.04 | 0.02093 |

Figure 3:
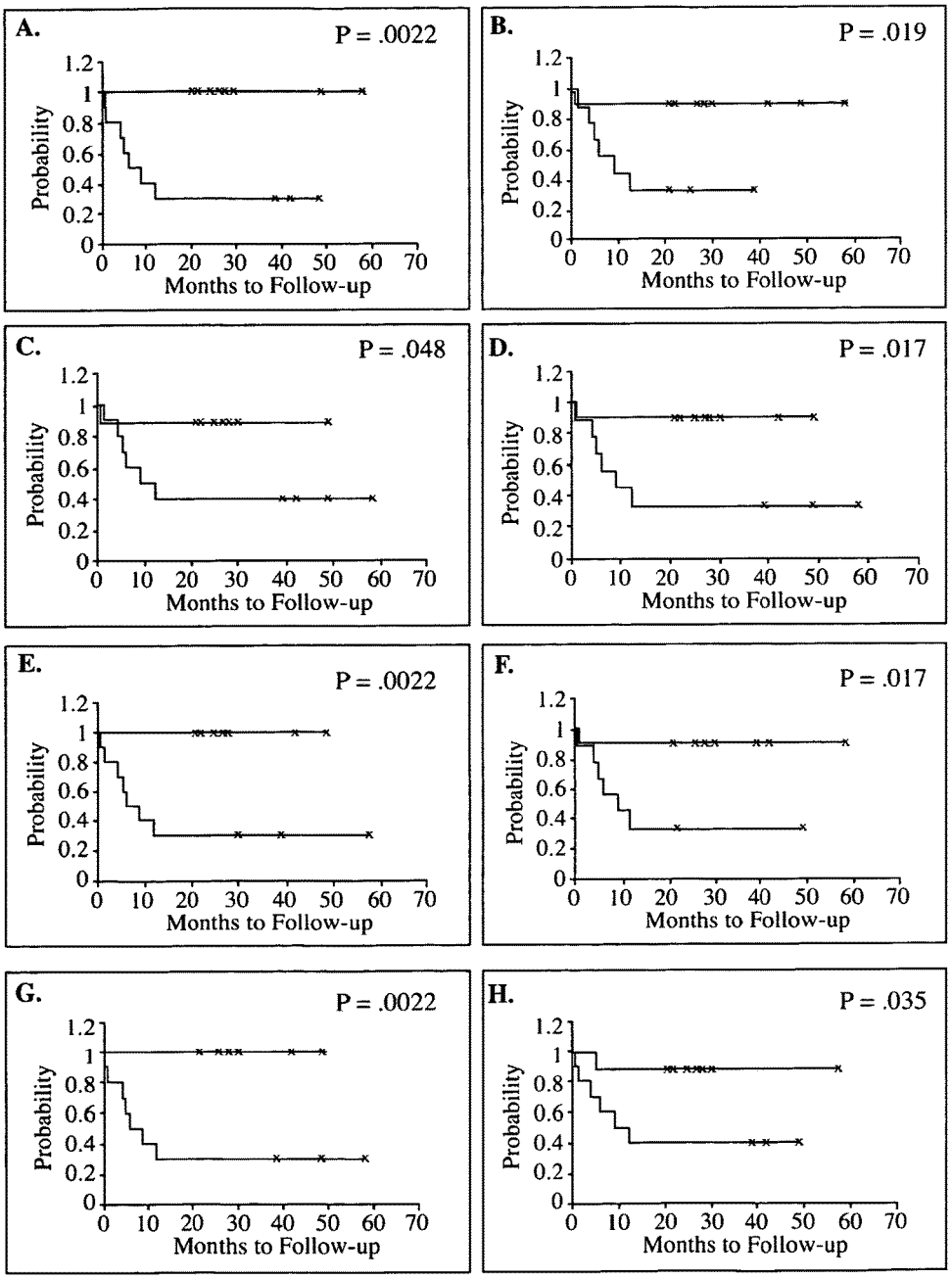
FIG. 3. Kaplan-Meier survival curves for 8 genes from whole blood samples that are predictive of graft loss. Genes include AHSA2 (FIG. 3A), IGHG1 (FIG. 3B), IFNAR2 (FIG. 3C), IGKC (FIG. 3D), HIST1H2BC (FIG. 3E), IL1R2 (FIG. 3F), MAPK1 (FIG. 3G), and MAPK9 (FIG. 3H).

The Kaplan-Meier survival curves for 8 of these genes are illustrated in FIG. 3. The genes in FIG. 3 include A) AHSA2, B) IGHG1, C) IFNAR2, D) IGKC, E) HIST1H2BC, F) IL1R2, G) MAPK1, and H) MAPK9.

The functional composition of genes associated with acute rejection, predicted by analysis of Gene Ontology annotations, is summarized in Table 5.

TABLE 5

| Gene Category | Genes | Genes on Array | EASE Score | Fisher Exact |
|---|---|---|---|---|
| defense response | 105 | 747 | 7.15E−12 | 3.35E−12 |
| response to stimulus/ acute phase response | 152 | 1482 | 0.00000108 | 7.24E−07 |
| apoptosis | 50 | 361 | 0.00000772 | 3.63E−06 |
| cell cycle | 71 | 597 | 0.0000174 | 9.84E−06 |
| cell proliferation | 96 | 899 | 0.0000403 | 0.0000256 |
| protein metabolism | 176 | 1941 | 0.000228 | 0.000172 |
| antigen presentation | 9 | 29 | 0.000707 | 0.000123 |
| cell growth and/or maintenance | 244 | 2887 | 0.000766 | 0.000623 |
| phosphorylation | 53 | 512 | 0.00539 | 0.00353 |
| protein modification | 84 | 902 | 0.00775 | 0.00545 |
| hemopoiesis | 10 | 53 | 0.0116 | 0.00374 |
| DNA replication | 17 | 122 | 0.0125 | 0.00571 |
| B-cell activation | 6 | 22 | 0.0171 | 0.00356 |

The full list of known genes (in ranked order) in whole blood that are predictive of graft loss following acute rejection is summarized in Table 1. Of the 81 cDNA clones identified to have the highest predictive power, 62 are of known function or assigned unique Unigene Cluster IDs. Similarly, the list of known genes identified in renal biopsies predictive of graft loss following acute rejection is summarized in Table 2 (including 30 unique genes of known function from the 50 cDNA associated clones).

IV. Generation of a Transplant Custom Expression Chip

TxChip

We have compiled the gene lists described in this document for AR and graft loss along with other expression-based markers identified to be associated with clinical outcomes and severity of:

1. Acute rejection—including markers associated with graft loss and/or rate of recovery of renal function following AR (Table 3);
2. Chronic allograft injury (chronic rejection) in blood (Table 3);
3. Immunosuppressive drug toxicity or adverse side effects including drug-induced hypertension (Table 3);
4. Age or body mass index associated genes that correlate with renal pathology or account for differences in recipient age-related graft acceptance (Table 3);
5. Immune tolerance markers in whole blood (Table 3);
6. Control genes for assessing sample quality (3'- to 5'-bias in probe location), sampling error in biopsy-based studies, cell surface markers, and normalizing genes for calibrating hybridization results;
7. Genes found in literature surveys with immune modulatory roles that may play a role in transplant outcomes (Table 3) to produce the list for a representative array having probes to genes listed in Table 3.

A. Test of Expression Uniformity Across a Pilot Study of Renal Biopsies.

In the identification of the gene markers described in this invention disclosure, we compared the expression across a set of 67 renal biopsies described in detail by our laboratory. A subset of the biopsy-generated gene expression markers was used clustered to compare expression profiles in patients with confirmed cases of DT, CAN, AR and no significant abnormality (Normal). These patients were on two very different immunosuppressant regimes, either steroid-based or steroid-free (clinical regiment previously described in (Sarwal et al., Transplantation (2001) 72:13-21) and Sarwal et al., Transplantation (2003) 76:1331-9).

FIG. 4 illustrates that the gene expression is generally uniform/consistent across the full clinical groups analyzed as the gene expression levels segregate well within patient groups. Further, within each group (DT, CAN, AR or Normal) expression levels of these marker genes are independent of immunosuppression use.

The 479 gene list of Table 3 comprises design and specification for a customized thematic Transplant Chip (TxChip V1) and full-length mRNA sequences for these genes are listed in Table 3. The gene listing is cross-indexed to the studies listed above. We observe a modest overlap in the list of informative genes. For example, expression levels of IGHM positively correlate with acute rejection risk and negatively correlate with immune tolerance. An advantage of having the full compilation of genes on a common platform is that new discoveries like this can be made in future studies.

It is evident that subject invention provides a convenient and effective way of determining whether a graft in a subject will survive, e.g., following acute rejection. As such, the subject invention provides a number of distinct benefits, including the ability to identify clinically relevant AR groups with differing therapeutic responses and prognosis, and allow for individualized treatment and monitoring. As such, the subject invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of evaluating [graft survival in a subject] *gene expression levels of at least two genes in a sample from a transplant recipient*, said method comprising:

*providing a sample from a transplant recipient; and*

[assessing] *measuring an amount of* expression of at least two genes in [a] *the* sample [from said subject to evaluate graft survival in said subject], wherein said at least two genes comprises [HIST1H2B] *HIST1H2BC* and IGHG3.

2. The method according to claim 1, wherein said expression of at least two genes is assessed by assaying said sample for a nucleic acid transcript of said gene.

3. The method according to claim 1, wherein said expression of at least two genes is assessed by assaying said sample for an expression product of said gene.

4. The method according to [any of] claim 1, wherein said sample is a blood sample.

5. The method according to claim 4, wherein said blood sample is a peripheral blood sample.

6. The method according to claim 1, wherein said sample is a tissue biopsy sample.

7. A method according to claim 1, wherein the method comprises: obtaining an expression profile for a sample from said subject.

[8. The method according to claim 7, wherein said expression profile is compared to a reference expression profile.]

9. The method according to claim [8] *7*, wherein said expression profile is a nucleic acid expression profile.

10. The method according to claim [8] *7*, wherein said expression profile comprises expression measurements for at least 5 different genes.

11. The method according to claim [8] *7*, wherein said expression profile is determined using a microarray.

12. The method according to claim 11, wherein said microarray is a genomic array.

13. A method of [managing post-transplantation therapy in a subject, said method] *treating a transplant recipient* comprising:

(a) [evaluating] *determining that a transplant recipient has a* graft survival [in said subject by a method according to claim 1; and] *phenotype by evaluating results previously obtained from a quantitative determination of nucleic acid expression levels of at least two genes in a sample from the transplant recipient, and*

*treating said transplant recipient by maintaining a current therapeutic regimen; or*

(b) determining [a post-transplantation therapy protocol based on said evaluation step (a);] *that a transplant recipient has a graft loss phenotype by evaluating results previously obtained from a quantitative determination of nucleic acid expression levels of at least two genes in a sample from the transplant recipient, and*

*treating said transplant recipient by increasing or decreasing a therapeutic regimen;*

*wherein, said evaluating comprises comparing said results to a reference nucleic acid expression profile comprising said at least two genes; and*

[to manage post-transplantation therapy in said subject] *wherein said at least two genes comprises HIST1H2BC and IGHG3.*

14. The method according to claim 13, wherein said subject is a human.

15. The method according to claim 1, wherein said at least two genes further comprises one or more genes selected from: AHSA2, TNFRSF10D, MAPK9, IFNAR2, TM4SF9, MIF, SCYE1, MAPK1, TGFBR3, IGKC, IL1R2 and IGL.

*16. The method of claim 7, wherein said expression profile comprises expression measurements for at least ten different genes.*

*17. A method of assaying gene expression in a blood sample from a graft recipient, the method comprising:*

*a) receiving a sample of blood from a patient that has received a graft; and*

*b) assaying the expression of at least two genes in the blood sample, wherein said at least two genes comprises HIST1H2BC and IGHG3.*

*18. The method according to claim 13, wherein the therapeutic regimen is an immunosuppressive therapy.*

*19. The method according to claim 13, comprising: determining that the transplant recipient has a graft loss pheno-*

*type that is calcineurin-inhibitor drug nephrotoxicity (DT); and decreasing an immunosuppressive therapy.*

*20. The method according to claim 13, comprising: (i) determining that the transplant recipient has a graft loss phenotype that is chronic allograft nephropathy (CAN); and (ii) increasing an immunosuppressive therapy, or changing an immunosuppressive therapy by administering a different immunosuppressive drug.*

*21. The method according to claim 1, further comprising measuring an amount of expression of control genes in the sample.*

* * * * *